(12) United States Patent
Matsumoto et al.

(10) Patent No.: US 7,115,757 B2
(45) Date of Patent: Oct. 3, 2006

(54) 1,2-DIOXETANE DERIVATIVES AND REAGENTS EMPLOYING THEM

(75) Inventors: Masakatsu Matsumoto, Tokyo (JP); Nobuko Watanabe, Kanagawa (JP); Masashi Yamada, Kanagawa (JP)

(73) Assignee: Tosoh Corporation, Shinnanyo (JP)

( * ) Notice: Subject to any disclaimer, the term of this patent is extended or adjusted under 35 U.S.C. 154(b) by 0 days.

(21) Appl. No.: 11/000,269

(22) Filed: Dec. 1, 2004

(65) Prior Publication Data

US 2005/0153365 A1 Jul. 14, 2005

Related U.S. Application Data

(62) Division of application No. 10/798,338, filed on Mar. 12, 2004, now Pat. No. 6,844,453, which is a division of application No. 10/382,853, filed on Mar. 7, 2003, now Pat. No. 6,747,160.

(30) Foreign Application Priority Data

| Mar. 8, 2002 | (JP) | ............................. 2002-064040 |
| Mar. 27, 2002 | (JP) | ............................. 2002-088380 |

(51) Int. Cl.
*C07D 307/93* (2006.01)
(52) U.S. Cl. ...................... 549/464; 549/510
(58) Field of Classification Search ................ 549/464, 549/510
See application file for complete search history.

(56) References Cited

U.S. PATENT DOCUMENTS

| 4,857,652 | A | 8/1989 | Schaap |
| 4,956,477 | A | 9/1990 | Bronstein et al. |
| 4,962,192 | A | 10/1990 | Schaap |
| 5,177,241 | A | 1/1993 | Bronstein et al. |
| 5,386,017 | A | 1/1995 | Schaap |
| 5,578,253 | A | 11/1996 | Schaap et al. |
| 5,603,868 | A | 2/1997 | Wang et al. |
| 5,607,625 | A | 3/1997 | Wang et al. |
| 5,625,077 | A | 4/1997 | Bronstein |
| 5,637,747 | A | 6/1997 | Bronstein et al. |
| 5,639,907 | A | 6/1997 | Bronstein et al. |
| 5,648,555 | A | 7/1997 | Bronstein et al. |
| 5,650,525 | A | 7/1997 | Matsumoto |
| 5,679,802 | A | 10/1997 | Bronstein et al. |
| 5,698,727 | A | 12/1997 | Matsumoto |
| 5,707,559 | A | 1/1998 | Schaap et al. |
| 5,731,445 | A | 3/1998 | Matsumoto et al. |
| 5,770,743 | A | 6/1998 | Schaap et al. |
| 5,780,249 | A | 7/1998 | Wang et al. |
| 5,795,987 | A | 8/1998 | Schaap et al. |
| 5,800,999 | A | 9/1998 | Bronstein et al. |
| 5,856,522 | A | 1/1999 | Bronstein et al. |
| 5,869,698 | A | 2/1999 | Schaap et al. |
| 5,877,333 | A | 3/1999 | Matsumoto et al. |
| 5,929,254 | A | 7/1999 | Matsumoto |
| 5,936,132 | A | 8/1999 | Matsumoto |
| 6,001,561 | A | 12/1999 | Wang et al. |
| 6,001,659 | A | 12/1999 | Wang et al. |
| 6,063,574 | A | 5/2000 | Bronstein et al. |
| 6,124,478 | A | 9/2000 | Bronstein et al. |
| 6,139,781 | A | 10/2000 | Wang et al. |
| 6,218,135 | B1 | 4/2001 | Matsumoto et al. |
| 6,228,653 | B1 | 5/2001 | Matsumoto et al. |
| 6,417,380 | B1 | 7/2002 | Bronstein et al. |
| 6,451,531 | B1 | 9/2002 | Bronstein et al. |
| 6,747,160 | B1 | 6/2004 | Matsumoto et al. |
| 2002/0106687 | A1 | 8/2002 | Bronstein et al. |
| 2002/0132365 | A1 | 9/2002 | Matsumoto et al. |

FOREIGN PATENT DOCUMENTS

| EP | 0779293 A1 | 6/1997 |
| JP | 8-245615 | 9/1996 |
| JP | 9-157271 | 6/1997 |

*Primary Examiner*—Taofiq Solola
(74) *Attorney, Agent, or Firm*—Oblon, Spivak, McClelland, Maier & Neustadt, P.C.

(57) ABSTRACT

A 1,2-dioxetane derivative of the formula (I):

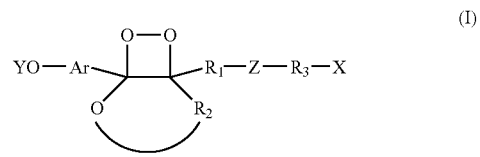

Figure 1:
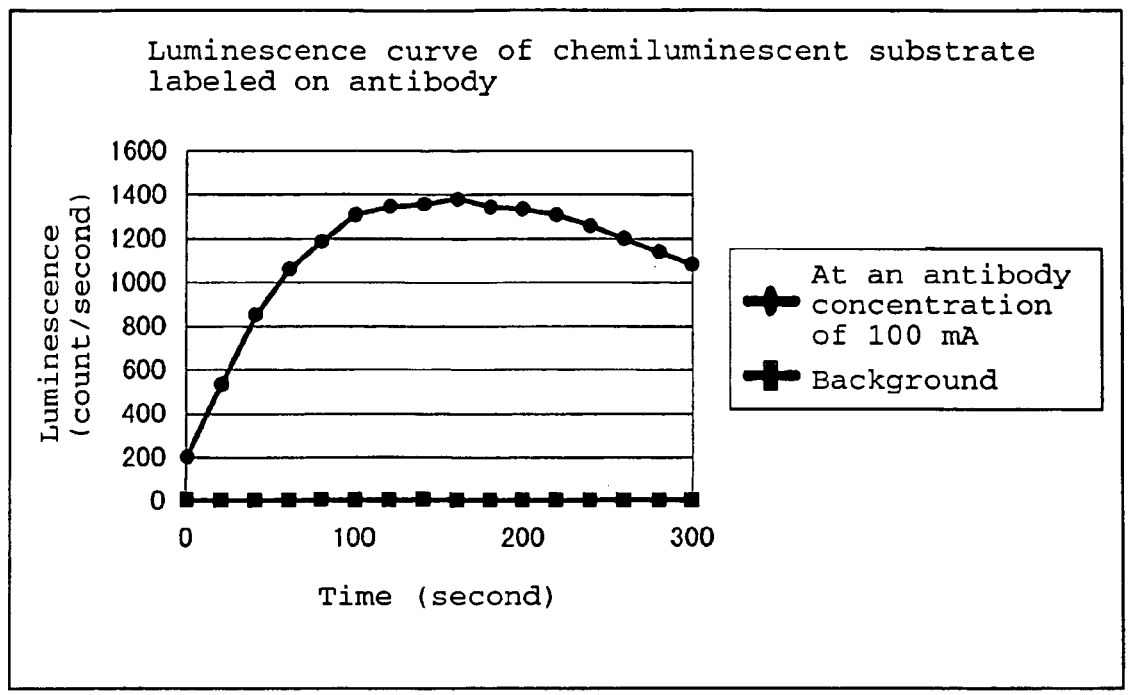

wherein Ar is an aryl group which may have an alkyl group, an aryl group, a halogen atom, an alkoxyl group, a carboxyl group, a formyl group, an alkyl ester, an aryl ester, an alkylketone, an arylketone or a hetero ring bonded thereto, X is a substituent capable of labeling an organic compound or a biological molecule, or an ester, Y is a hydrogen atom, an acyl group or a group of the formula —Si($R_4R_5R_6$) (wherein each of $R_4$, $R_5$ and $R_6$ which are independent of one another, is an alkyl group or an aryl group), Z is an alkyl group, an aryl group, an oxygen atom, a sulfur atom, a carbonyl group, —(CO)—O—, —O—(CO)—, —NH—, —NH—CO—, —CO—NH—, —OSi($R_7R_8$)— (wherein each of $R_7$ and $R_8$ which are independent of each other, is an alkyl group or aryl group) or a group of the formula —($R_9R_{10}$)SiO— (wherein each of $R_9$ and $R_{10}$ which are independent of each other, is an alkyl group or an aryl group), each of $R_1$ and $R_2$ is an alkyl group or an aryl group, and $R_3$ is a spacer.

9 Claims, 1 Drawing Sheet

1,2-DIOXETANE DERIVATIVES AND REAGENTS EMPLOYING THEM

The present invention relates to 1,2-dioxetane derivatives. The 1,2-dioxetane derivatives of the present invention are compounds which are capable of inducing chemiluminescence and can be used, for example, as substrates for immunoassay.

Heretofore, various 1,2-dioxetane derivatives have been synthesized, and it is known that compounds having a spiroadamantyl group bonded at the 3-position, are useful as chemiluminescent substrates (see, for example, JP-B-5-21918, and JP-B-5-45590) Further, as produced by the present inventors, various compounds are known (see, for example, JP-A-8-245615, JP-A-8-169885, JP-A-8-165287 and JP-A-2002-338576). These 1,2-dioxetane derivatives have an enzyme recognition site such as a phosphate ester group and will be triggered by an enzyme to produce luminescence. A series of such compounds are useful for a method wherein the activities of an enzyme labeled on an antigen or antibody adsorbed on a solid phase after an immunoreaction, are detected by a chemiluminescent reaction. In such a method, a 1,2-dioxetane solution is added to the measuring system, whereby even in a case no enzyme is present, luminescence by a heat or by a non-enzymatic decomposition reaction of e.g. a trace amount of impurities, will be detected, which leads to a rise of the background. Such a rise of the background is substantially influential to the detection sensitivity and thus is problematic.

Therefore, various compounds have been synthesized (see, for example, Japanese Patent 2,572,171, JP-A-08-502968 and JP-A-2002-508654), but the low stability of such dioxetane compounds themselves has still remained as a problem to be solved.

As mentioned above, various studies have been made with respect to 1,2-dioxetane derivatives, and various compounds have been produced. However, for such compounds to be useful in the fields of e.g. clinical tests, the compounds themselves are required to be stable and easy to handle and to have a performance to provide a low background for measurement to present high sensitivity. Accordingly, it has been desired to develop a compound superior to conventional compounds.

Under these circumstances, the present inventors have conducted an extensive study to develop a compound which is superior to conventional compounds and as a result, have succeeded in synthesizing a 1,2-dioxetane derivative which has a stable structure and is able to reduce the background for the measurement by e.g. an immunoassay and which can be labeled to an organic compound or a biological molecule. The present invention has been accomplished on the basis of this discovery.

Namely, the present invention provides a 1,2-dioxetane derivative of the formula (I):

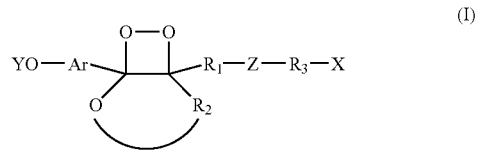

wherein Ar is an aryl group which may have an alkyl group, an aryl group, a halogen atom, an alkoxyl group, a carboxyl group, a formyl group, an alkyl ester, an aryl ester, an alkylketone, an arylketone or a hetero ring bonded thereto, X is a substituent capable of labeling an organic compound or a biological molecule, or an ester, Y is a hydrogen atom, an acyl group or a group of the formula —Si($R_4R_5R_6$) (wherein each of $R_4$, $R_5$ and $R_6$ which are independent of one another, is an alkyl group or an aryl group), Z is an alkyl group, an aryl group, an oxygen atom, a sulfur atom, a carbonyl group, —(CO)—O—, —O—(CO)—, —NH—, —NH—CO—, —CO—NH—, —OSi($R_7R_8$)— (wherein each of $R_7$ and $R_8$ which are independent of each other, is an alkyl group or aryl group) or a group of the formula —($R_9R_{10}$)SiO— (wherein each of $R_9$ and $R_{10}$ which are independent of each other, is an alkyl group or an aryl group), each of $R_1$ and $R_2$ is an alkyl group or an aryl group, and $R_3$ is a spacer.

Further, the present invention provides a 1,2-dioxetane derivative of the formula (III):

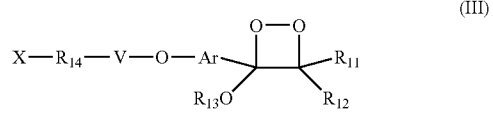

wherein Ar is an aryl group which may have an alkyl group, an aryl group, a halogen atom, an alkoxyl group, a carboxyl group, a formyl group, an alkyl ester, an aryl ester, an alkylketone, an arylketone or a hetero ring bonded thereto, X is a substituent capable of labeling an organic compound or a biological molecule, or an ester, V is a carbonyl group or a group of the formula —Si($R_{15}R_{16}$)— (wherein each of $R_{15}$ and $R_{16}$ which are independent of each other, is an alkyl group or aryl group), each of $R_{11}$ and $R_{12}$ which are independent of each other, is a hydrogen atom, an alkyl group or an aryl group, or $R_{11}$ and $R_{12}$ may together form a cyclic or polycyclic organic ring group spiro-bonded to the dioxetane ring, $R_{13}$ is an alkyl group or an aryl group, or $R_{13}$ and $R_{11}$, or $R_{13}$ and $R_{12}$, may together form a condensed ring containing the dioxetane ring and a hetero atom, and $R_{14}$ is a spacer.

Still further, the present invention provides a chemiluminescent reagent which contains the above 1,2-dioxetane derivative. Still further, the present invention provides an immunoassay reagent wherein the above 1,2-dioxetane derivative is bonded to a substance having a specific affinity via a part of its X or W.

In the accompanying drawing,

FIG. 1 is a graph showing a luminescence curve obtained in Example 38.

Now, the present invention will be described in detail with reference to the preferred embodiments.

In this specification, "an alkyl group" means a $C_{1-20}$ straight chain or branched alkyl group which may have a substituent, and it may, for example, be a straight chain group such as methyl, ethyl, propyl, butyl, pentyl, hexyl, heptyl, octyl, nonyl, decyl, undecyl, dodecyl, tetradecyl, pentadecyl, hexadecyl, heptadecyl, octadecyl, nonadecyl or icosanyl, or a group in which such an alkyl group is branched. The substituent which such an alkyl group may have, is, for example, a hydroxyl group, an alkoxyl group or an aryl group.

In this specification, "an alkoxyl group" may, for example, be one having from 1 to 5 $C_{1-20}$ alkoxyl groups bonded in a straight chain form or in a branched form, such as methoxy, ethoxy, propoxy, butoxy, pentyloxy, hexyloxy, methoxyethoxy, methoxypropoxy, ethoxyethoxy, ethoxypropoxy or methoxyethoxyethoxy. In this specification, "an aryl group" may, for example, be a $C_{6-20}$ aromatic hydrocarbon group such as phenyl or naphthyl, or a heteroaryl group having from 1 to 5 nitrogen atoms, oxygen atoms or sulfur atoms in a ring, such as furyl, thienyl or pyridyl.

In this specification, "an acyl group" may, for example, be a formyl group, an acetyl group, a succinyl group, a benzoyl group, a 1-naphthoyl group or a 2-naphthoyl group. Further, in this specification, "a cyclic organic ring group" is a $C_{5-10}$ cyclic alkylene such as cyclohexyl or cycloheptyl, and "a polycyclic organic ring group" is a $C_{6-30}$ polycyclic alkylene which may optionally be substituted by from 1 to 10 groups independently selected from $C_{1-10}$ alkyl, $C_{1-10}$ alkoxyl, halogen and halo-$C_{1-10}$ alkyl, such as an adamantyl group or a bicyclo[2.2.1]heptyl group. Further, a halogen atom, an alkyl group, an aryl group, a cyano group, an amide group, an alkoxyl group or a carboxyl group may be bonded to optional carbon of such a polycyclic organic ring group.

Further, in this specification, "an hetero ring" may, for example, be furan, thiophene, pyrrol, oxazole, isooxazole, thiazole, isothiazole, imidazole, pyrazole, furazane, pyran, pyridine, pyridadine, pyrimidine or pyradine. "A halogen atom" may, for example, be fluorine, chlorine or bromine.

X is a substituent capable of labeling an organic compound or a biological molecule, or an ester. The substituent capable of labeling an organic compound or a biological molecule, may, for example, be a carboxyl group, a succinimidoxy substituent, an acid chloride, an amino group, a maleimide group or a succinimidoxycarbonyl group, and the ester may, for example, be a $C_{1-6}$ alkyl ester. Each of $R_3$ and $R_{14}$ is a spacer and may, for example, be —$(CH_2)_n$— or —$(CH_2)_n NH$— (wherein n is an integer of from 1 to 20).

Further, in the formula (III), the case wherein $R_{13}$ and $R_{11}$, or $R_{13}$ and $R_{12}$, together form a condensed ring containing the dioxetane ring and a hetero atom, may, for example, be a condensed ring of the dioxetane ring and a furan ring, or a condensed ring of the dioxetane ring and a pyran ring.

Among those of the formula (I), preferred is a 1,2-dioxetane derivative of the formula (II):

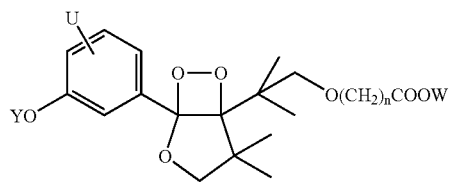

(II)

wherein Y is the same as Y in the formula (I), n is an integer of from 1 to 20, W is a hydrogen atom, an alkyl group or a succinimido substituent, and U is a hydrogen atom, an alkyl group, an aryl group, a halogen atom, an alkoxyl group, a carboxyl group, a formyl group, an alkyl ester, an aryl ester, an alkylketone, an arylketone or a hetero ring. More preferably, U is a hydrogen atom, n is from 1 to 15, W is a hydrogen atom, a $C_{1-6}$ alkyl group such as an ethyl group, or a succinimido, and Y is a $C_{1-6}$ acyl group or —$Si(R_4R_5R_6)$ (particularly each of $R_4$, $R_5$ and $R_6$ is a $C_{1-6}$ alkyl group).

Among those of the formula (III), preferred is a 1,2-dioxetane derivative of the formula (IV):

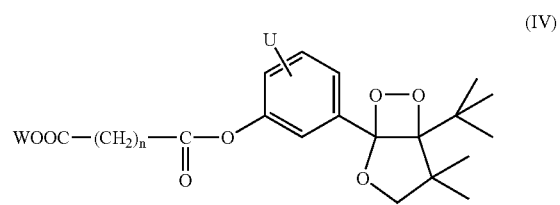

(IV)

wherein n is an integer of from 1 to 20, W is a hydrogen atom, an alkyl group or a succinimido substituent, and U is a hydrogen atom, an alkyl group, an aryl group, a halogen atom, an alkoxyl group, a carboxyl group, a formyl group, an alkyl ester, an aryl ester, an alkylketone, an arylketone or a hetero ring. More preferably, U is a hetero ring, particularly an isooxazole ring which may have a substituent such as $CF_3$, n is from 1 to 6, and W is a succinimido group, a hydrogen atom or an alkyl group.

The following process may, for example, be mentioned as a production process wherein the compound of the formula (I) is a dihydrofuran derivative.

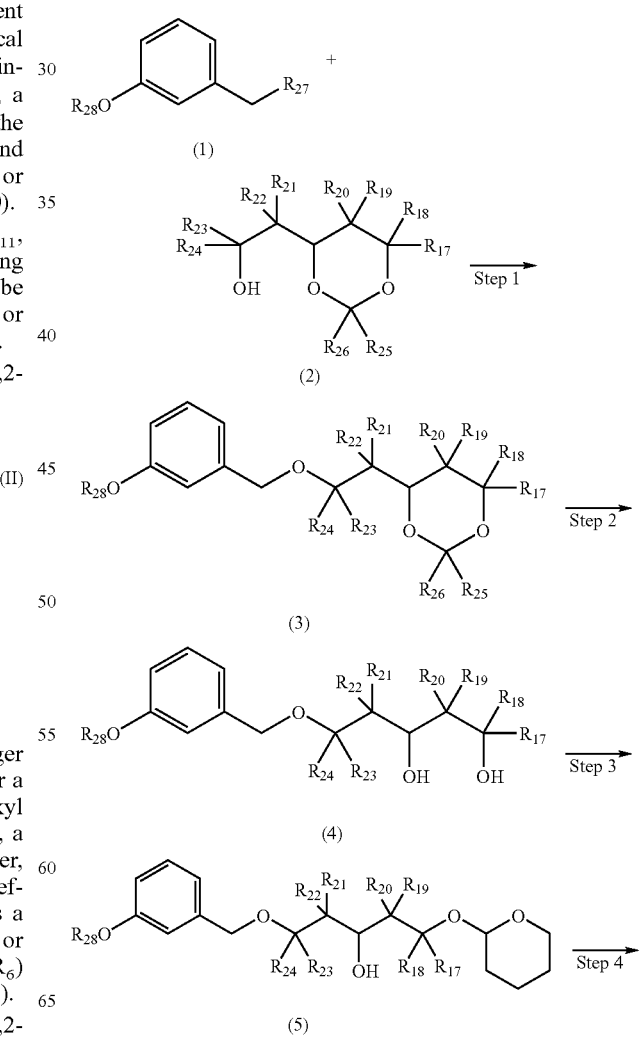

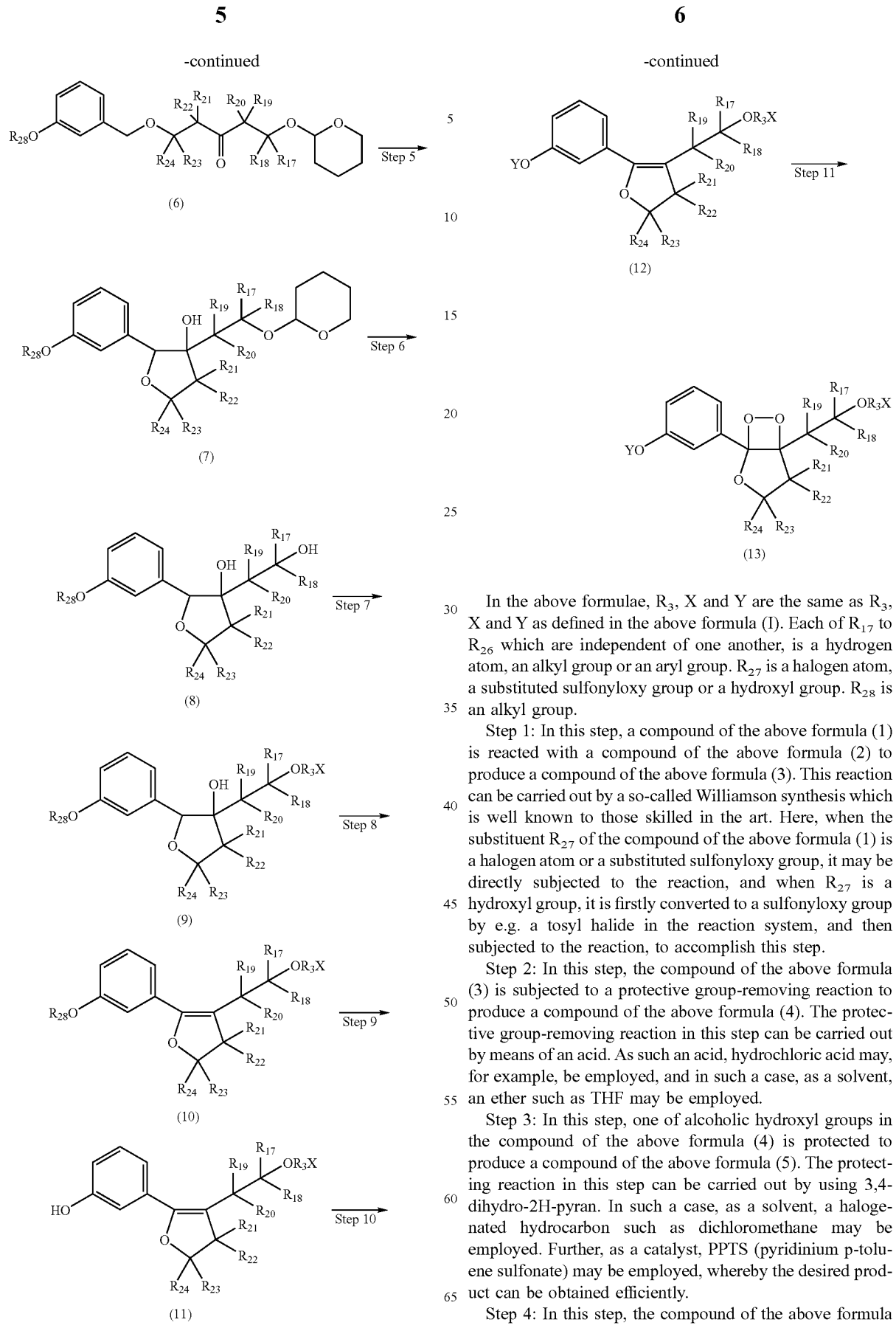

In the above formulae, $R_3$, X and Y are the same as $R_3$, X and Y as defined in the above formula (I). Each of $R_{17}$ to $R_{26}$ which are independent of one another, is a hydrogen atom, an alkyl group or an aryl group. $R_{27}$ is a halogen atom, a substituted sulfonyloxy group or a hydroxyl group. $R_{28}$ is an alkyl group.

Step 1: In this step, a compound of the above formula (1) is reacted with a compound of the above formula (2) to produce a compound of the above formula (3). This reaction can be carried out by a so-called Williamson synthesis which is well known to those skilled in the art. Here, when the substituent $R_{27}$ of the compound of the above formula (1) is a halogen atom or a substituted sulfonyloxy group, it may be directly subjected to the reaction, and when $R_{27}$ is a hydroxyl group, it is firstly converted to a sulfonyloxy group by e.g. a tosyl halide in the reaction system, and then subjected to the reaction, to accomplish this step.

Step 2: In this step, the compound of the above formula (3) is subjected to a protective group-removing reaction to produce a compound of the above formula (4). The protective group-removing reaction in this step can be carried out by means of an acid. As such an acid, hydrochloric acid may, for example, be employed, and in such a case, as a solvent, an ether such as THF may be employed.

Step 3: In this step, one of alcoholic hydroxyl groups in the compound of the above formula (4) is protected to produce a compound of the above formula (5). The protecting reaction in this step can be carried out by using 3,4-dihydro-2H-pyran. In such a case, as a solvent, a halogenated hydrocarbon such as dichloromethane may be employed. Further, as a catalyst, PPTS (pyridinium p-toluene sulfonate) may be employed, whereby the desired product can be obtained efficiently.

Step 4: In this step, the compound of the above formula (5) is oxidized to produce a compound of the above formula (6). The oxidation in this step can be carried out by using a chromium oxidizing agent or an activating agent. Such a chromium oxidizing agent may, for example, be pyridinium chlorochromate (PCC) or pyridinium dichlorochromate (PDC). In such a case, as a solvent, a halogenated hydrocarbon such as dichloromethane may be employed. Whereas, when the above-mentioned activating agent is to be used, the reaction may be carried out in a combination with a solvent, such as a Py.SO$_3$/triethylamine/DMSO system or an Ac$_2$O/DMSO system.

Step 5: In this step, the compound of the above formula (6) is subjected to ring closure to produce a compound of the above formula (7). The reaction is carried out by using a base such as a lithium salt of a secondary amine such as lithium diisopropylamide, or t-butoxy potassium. As a solvent, an organic solvent such as THF or DMSO may be employed, and it is preferred to carry out the reaction from 0° C. to room temperature for from 1 to 5 hours.

Step 6: In this step, the compound of the above formula (7) is subjected to a protective group-removing reaction to produce a compound of the above formula (8). The group-removing reaction in this step can be carried out by using an acid. As such an acid, hydrochloric acid may, for example, be employed, and in such a case, as a solvent, an alcohol such as methanol can be used.

Step 7: In this step, the compound of the above formula (8) is reacted with a compound having a R$_3$X substituent to produce a compound of the above formula (9). This reaction can be accomplished by a so-called Williamson synthesis which is well known to those skilled in the art.

Step 8: In this step, the compound of the above formula (9) is dehydrated to produce a compound of the above formula (10). For the reaction, thionyl chloride may be reacted in the presence of a base such as pyridine, or an acid such as phosphoric acid or p-toluene sulfonic acid may be used as a catalyst. As a solvent, a halogenated hydrocarbon such as dichloromethane, or an aromatic hydrocarbon such as toluene, may be employed, and the solvent may suitably be selected for use depending upon the reagent to be reacted.

Step 9: In this step, the compound of the above formula (10) is subjected to a protective group-removing reaction to produce a compound of the above formula (11). In the case of a compound represented by a methoxy group or a benzyloxy group, this reaction can be carried out by a method well known to those skilled in the art, i.e. by reacting it with an anion of an alkylthiol, or by subjecting it to a hydrogenation reaction. Either reaction may be selected for use depending upon the group to be removed.

Step 10: In this step, a compound which can be removed in the presence of fluorine ions or under an alkaline condition, is introduced to the phenolic hydroxyl group of the compound of the above formula (11) to produce a compound of the above formula (12). In order to form a group represented by an alkyl ester, an aryl ester or —OSi(R$_4$R$_5$R$_6$) (wherein each of R$_4$, R$_5$ and R$_6$ which are independent of one another, is an alkyl group or an aryl group), the corresponding acid anhydride or halogenated silane compound is reacted to produce the compound of the above formula (12).

Step 11: In this step, the compound of the above formula (12) is reacted with singlet oxygen to produce a 1,2-dioxetane derivative of the above formula (13). The reaction with singlet oxygen can be accomplished by carrying out visible light irradiation in an oxygen atmosphere in the co-existence of a photosensitizer such as Methylene Blue, Rose Bengale or tetraphenyl porphine (TPP). Here, as a solvent, a halogenated hydrocarbon such as dichloromethane, dichloroethane or carbon tetrachloride, or an alcohol such as methanol or ethanol, may be employed. Further, the reaction is preferably carried out at a temperature of from −80° C. to room temperature.

The compound of the above formula (III) may be produced, for example, by reacting an acid anhydride to a compound obtained by the method disclosed in e.g. JP-A-2002-338576.

The 1,2-dioxetane derivative of the above formula (I) or (III) of the present invention will be decomposed into a carbonyl compound accompanying chemiluminescence in the presence of fluorine ions or under an alkaline condition. Accordingly, such a derivative can be used as a chemiluminescent reagent and can be used, for example, in an immunoassay, a chemical detecting method, a nucleotide probe method, etc.

Particularly, the 1,2-dioxetane derivative of the formula (I) or (III) of the present invention can be used as an immunoassay reagent by bonding it to a substance having a specific affinity via a part of its X or W. An immunoassay employing such an immunoassay reagent may, for example, be carried out by a step of mixing the immunoassay reagent of the present invention and a test sample containing a substance to be detected and reacting them for a prescribed period of time to bond the substance to be detected in the sample with the substance having a specific affinity thereto, and a step of obtaining the amount of the substance having the specific affinity, which was bonded or not bonded. Since the portion corresponding to the 1,2-dioxetane derivative constituting the immunoassay reagent of the present invention will decompose accompanying a chemiluminescence in the presence of fluorine ions or under an alkaline condition, the above-mentioned step of obtaining the amount of the substance having a specific affinity, which was bonded or not bonded, can be carried out by measuring the intensity of the luminescence. The intensity of the luminescence in such a case, increases in proportion to the amount of the portion corresponding to the 1,2-dioxetane derivative.

Substances to be detected in the above immunoassay include, for example, hormones such as hCG, TSH and LH, cancer-related substances such as AFP or CEA, viral antigens and antibodies, such as HIV or HTLV-I, and nucleic acids (DNA, RNA). Further, the substance having a specific affinity, constituting the immunoassay reagent of the present invention, is one having a specific affinity to the substance to be detected, and it may, for example, be an antibody or a receptor.

Now, the present invention will be described in further detail with reference to Examples. However, it should be understood that the present invention is by no means restricted to such specific Examples.

EXAMPLE 1

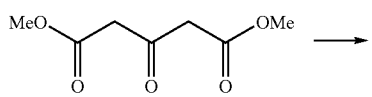

[1]

-continued

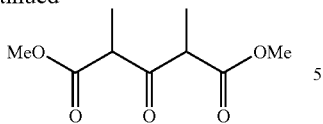

[2]

In a nitrogen atmosphere at 0° C., to a DMF (100 mL) having potassium carbonate (73.2 g, 529.6 mmol, 3 eq.) suspended, dimethyl 1,3-acetondicarboxylate (compound (1)) (30.9 g, 177.4 mmol) dissolved in DMF (25 mL) was dropwise added over a period of 12 minutes, and then, methyl iodide (33 mL, 530.1 mmol, 3 eq.) dissolved in DMF (20 mL) was dropwise added over a period of 40 minutes. The reaction solution was gradually returned to room temperature and stirred, and DMF (40 mL+50 mL) was added, followed by stirring for one day. This reaction solution was put into water and extracted with ethyl acetate. The aqueous layer was again extracted with ethyl acetate, and the extract was put together with the previous organic layer, followed by washing with a saturated sodium chloride aqueous solution. The organic layer was dried over anhydrous magnesium sulfate and concentrated to obtain the dimethyl 1,3-dimethyl-2-oxo-1,3-propanedicarboxylate (compound (2)) as a yellow oil (39.1 g). This product was used for the subsequent reaction without purification.

EXAMPLE 2

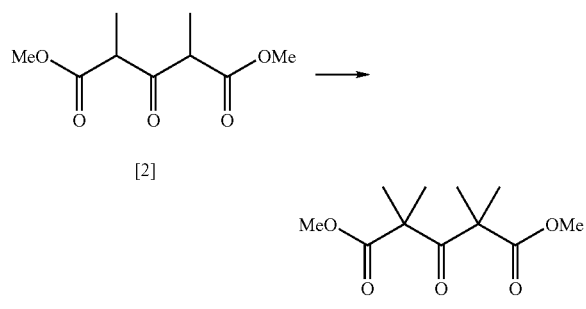

In a nitrogen atmosphere at 0° C., to a THF (100 mL) solution having 60% sodium hydride (17.9 g, 447.0 mmol, 2.6 eq.) suspended, the crude product (39.1 g) of dimethyl 1,3-dimethyl-2-oxo-1,3-propanedicarboxylate (compound (2)) dissolved in THF (50 mL), was dropwise added over a period of 45 minutes, followed by stirring for 30 minutes. Then, methyl iodide (33 mL, 530.1 mmol, 3 eq.) dissolved in THF (50 mL) was dropwise added over a period of 50 minutes, and the solution was gradually returned to room temperature and stirred for one day. This reaction solution was put into water and extracted with ethyl acetate. The aqueous layer was again extracted with ethyl acetate, and the extract was put together with the previous organic layer, followed by washing with a saturated sodium thiosulfate aqueous solution and a saturated sodium chloride aqueous solution. The organic layer was dried over anhydrous magnesium sulfate and concentrated to obtain the desired dimethyl 1,1,3,3-tetramethyl-2-oxo-1,3-propanedicarboxylate (compound (3)) as a yellow oil (42.9 g). This product was used for the subsequent reaction without purification.

EXAMPLE 3

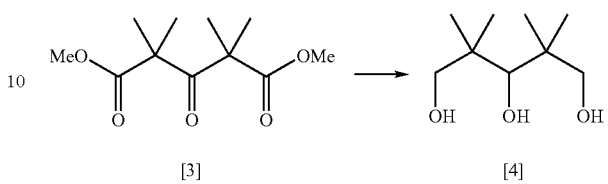

In a nitrogen atmosphere at 0° C., to a THF (150 mL) solution having lithium aluminum hydride (10.2 g, 268.2 mmol, 1.5 eq.) suspended, the crude product (42.9 g) of dimethyl 1,1,3,3-tetramethyl-2-oxo-1,3-propanedicarboxylate (compound (3)) dissolved in THF (50 mL), was dropwise added, and the solution was gradually returned to room temperature and stirred for one day. To this reaction solution, water (10 mL) dissolved in THF (10 mL) was added for quenching. This reaction solution was put into a 6N hydrochloric acid aqueous solution and extracted with ethyl acetate. The aqueous layer was again extracted with ethyl acetate, and the extract was put together with the previous organic layer, followed by washing with a saturated sodium chloride aqueous solution. The organic layer was dried over anhydrous magnesium sulfate and concentrated to obtain a residue as a yellow solid (28.7 g). This residue was rinsed with hexane to obtain a yellow solid (19.2 g, 109.2 mmol, 61.6%) of the desired 2,2,4,4-tetramethylpentan-1,3,5-triol (compound (4)) and a concentrate (8.98 g) of the filtrate. The concentrate of the filtrate was subjected to silica gel column chromatography with a developing solvent (ethyl acetate: hexane=1:3). As a result, a yellow solid (2.14 g, 12.13 mmol, 6.8%) was further obtained (the total yield of the compound (4): 68.4%).

Colorless needle crystal (mp. 61.1 to 61.5° C.)

$^1$H-NMR (400 MHz, CDCl$_3$): $\delta_H$ 1.00 (s, 6H). 1.09 (s, 6H), 2.95 (br, 2H), 3.47 (d, J=10, 6 Hz, 2H). 3.52 (d, J=10, 6 Hz, 2H), 3.64 (s, 12), 4.25 (br, 1H) ppm $^{13}$C-NMR (125 MHz, CDCl$_3$): $\delta_C$ 20.3, 24.7, 40.3, 75.4, 85.7 ppm IR (KBr): 3354, 2954, 2878, 1028 cm$^{-1}$ MASS (EI, 70 ev, m/z, %): 176 (M$^+$, trace), 128 (8), 103 (38), 97 (35), 85 (24), 73 (36) 58 (2) 54 (100).

EXAMPLE 4

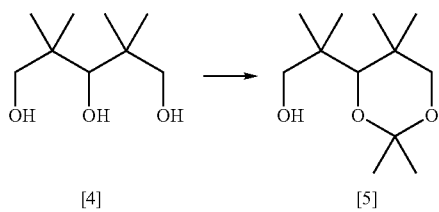

At room temperature, to a dichloromethane (200 mL) solution having 2,2,4,4-tetramethylpentan-1,3,5-triol (compound (4)) (24.7 g, 139.9 mmol) dissolved, acetone dimethylacetal (18 mL, 146.4 mmol, 1.1 eq.) was added, and then pyridinium p-toluene sulfonate (3.62 g, 13.99 mmol, 0.1 eq.) was added, followed by stirring for one day. This reaction solution was put into a saturated sodium hydrogencarbonate aqueous solution and extracted with ethyl acetate. The aqueous layer was again extracted with ethyl acetate, and the extract was put together with the previous organic layer, followed by washing with a saturated sodium chloride aqueous solution. The organic layer was dried over anhydrous magnesium sulfate and concentrated to obtain a residue as a yellow oil (31.2 g). This residue was subjected to silica gel column chromatography with a developing solvent (ethyl acetate:hexane=1:4). As a result, the desired 2-methyl-2-(2,2,5,5-tetramethyl-[1,3]dioxane-4-yl)-propan-1-ol (compound (5)) was obtained as a colorless oil (27.3 g, 126.3 mmol, 90.3%).

$^1$H-NMR (400 MHz, CDCl$_3$): $\delta_H$ 0.89 (s, 3H), 1.02 (s, 3H), 1.02 (s, 3H), 1.21 (s, 3H), 1.42 (s, 3H), 1.42 (s, 3H), 3.01 (d, J=5.2 Hz, 1H), 3.11 (d, J=11.5 Hz, 1H), 3.33 (d d, J=10.7 and 5.2 Hz, 1H), 3.54 (d, J=11.5 Hz, 1H), 3.54 (dd, J=10.7 and 5.2 Hz, 1H), 3.59 (s, 1H) ppm $^{13}$C-NMR (100 MHz, CDCl$_3$): $\delta_C$ 18.7, 20.3, 21.2, 24.1, 24.5, 29.0, 35.4, 40.2, 73.0, 74.4, 83.2, 98.5 ppm IR (liquid film): 2994, 2858, 1601, 1462, 1264, 1044 cm$^{-1}$.

EXAMPLE 5

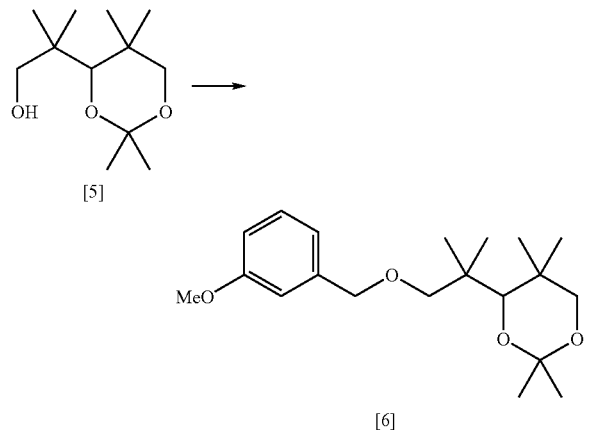

In a nitrogen atmosphere at 0° C., to a THF (30 mL) solution having 60% sodium hydride (968 mg, 24.00 mmol, 1.09 eq.) suspended, a THF (20 mL) solution having 2-methyl-2-(2,2,5,5-tetramethyl-[1,3]dioxane-4-yl)-propan-1-ol (compound (5)) (4.76 g, 21.98 mmol) dissolved, was dropwise added over a period of 15 minutes and 3-methoxybenzyl chloride (3.3 mL, 22.73 mmol, 1.03 eq.) was added. Then, TMF (5 mL) was added, and the solution was gradually returned to room temperature and heated at 50° C. and stirred for two hours. To this reaction solution, water was put, followed by extraction with a saturated ammonium chloride aqueous solution and ethyl acetate. The aqueous layer was again extracted with ethyl acetate, and the extract was put together with the previous organic layer, followed by washing with a saturated sodium chloride aqueous solution. The organic layer was dried over anhydrous magnesium sulfate and concentrated to obtain a residue as a yellow oil (7.67 g). This residue was subjected to silica gel column chromatography with a developing solvent (ethyl acetate: hexane=1:10). As a result, the desired 4-[2-(3-methoxybenziloxy)-1,1-dimethylethyl]-2,2,5,5-tetramethyl-[1,3]dioxane (compound (6)) was obtained as a colorless oil (6.62 g, 19.68 mmol, 89.6%).

$^1$H-NMR (400 MHz, CDCl$_3$): $\delta_H$ 0.88 (s, 3H), 0.95 (s, 3H), 1.05 (s, 3H), 1.14 (s, 3H), 1.34 (s, 3H), 1.37 (s, 3H), 3.01 (d, J=8.6 Hz, 1H), 3.08 (d, J=11.5 Hz, 1H), 3.37 (d, J=8.6 Hz, 1H), 3.51 (d, J=11.5 Hz, 1H), 3.65 (s, 1H), 3.81 (s, 3H), 4.42 (d, J=12.9 Hz, 1H), 4.47 (d, J=12.9 Hz, 1H), 6.82 (d with fine coupling, J=8.1 Hz, 1H). 6.90–6.91 (m, 2H), 7.25 (t, J=8.1 Hz, 1H) ppm $^{13}$C-NMR (100 MHz, CDCl$_3$): $\delta_C$ 19.1, 21.0, 21.9, 23.4, 24.3, 35.4, 40.5, 55.1, 72.9, 74.7, 78.5, 98.4, 112.7, 119.5, 129.1, 140.5, 159.5 ppm.

IR (liquid film): 3441, 2990, 2954, 2873, 1164, 1010, 938 cm$^{-1}$

MASS (EI, 70 ev, m/z, %): 336 (M$^+$, 8), 321 (6), 278 (9), 222 (55), 194 (5), 137 (36), 121 (100 ), 97 (12), 58 (55).

EXAMPLE 6

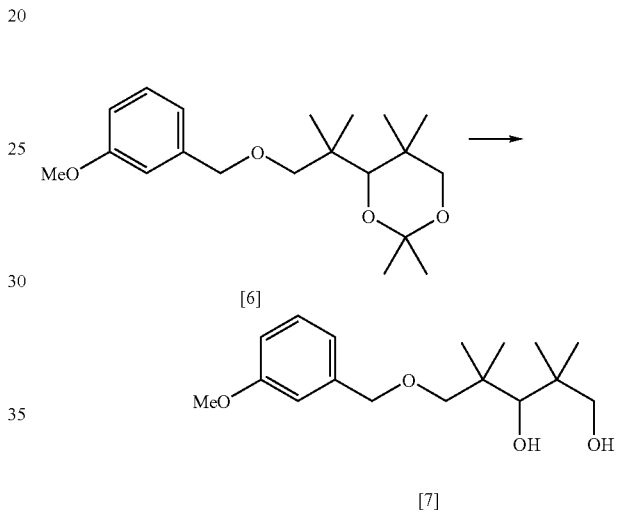

At room temperature, a THF (120 mL) solution having 4-[2-(3-methoxybenziloxy)-1,1-dimethylethyl]-2,2,5,5-tetramethyl-[1,3]dioxane (compound (6)) (15.6 g, 46.34 mmol) dissolved, a 3N hydrochloric acid aqueous solution (15 mL) was added, and the mixture was refluxed at 80° C. for 6 hours and 40 minutes. The reaction solution was put into a saturated sodium hydrogencarbonate aqueous solution and extracted with ethyl acetate. The aqueous layer was again extracted with ethyl acetate, and the extract was put together with the previous organic layer, followed by washing with a saturated sodium chloride aqueous solution. The organic layer was dried over anhydrous magnesium sulfate and concentrated to obtain a residue as a yellow oil (14.2 g). This residue was subjected to silica gel column chromatography with a developing solvent (ethyl acetate:hexane=1:7). As a result, the desired 5-(3-methoxybenzyloxy)-2,2,4,4-tetramethylpentan-1,3-diol (compound (7)) as a colorless oil (11.5 g, 38.68 mmol, 83.5%).

$^1$H-NMR (400 MHz, CDCl$_3$): $\delta_H$ 0.98 (s, 3H), 1.02 (s, 3H), 1.06 (s, 3H), 1.11 (s, 3H), 3.33 (s, 2H), 3.33–3.59 (m, 4H), 3.82 (s, 3H), 4.26 (br-s, 1H), 4.49 (s, 2H), 6.84–6.89 (m, 3H), 7.25–7.29 (m, 1H) ppm $^{13}$C-NMR (125 MHz, CDCl$_3$): $\delta_C$ 20.1, 21.1, 24.7, 25.0, 40.4, 40.4, 55.1, 73.6, 75.4, 83.0, 85.3, 112.9, 113.3, 120.0, 129.5, 139.0, 159.7 ppm IR (liquid film): 3415, 2957, 1600, 1266, 1155, 1079, 782 cm$^{-1}$ MASS (EI, 70 ev, m/z, %): 296 (M+, 19), 222 (8), 138 (94), 121 (100), 109 (8); 73 (10).

EXAMPLE 7

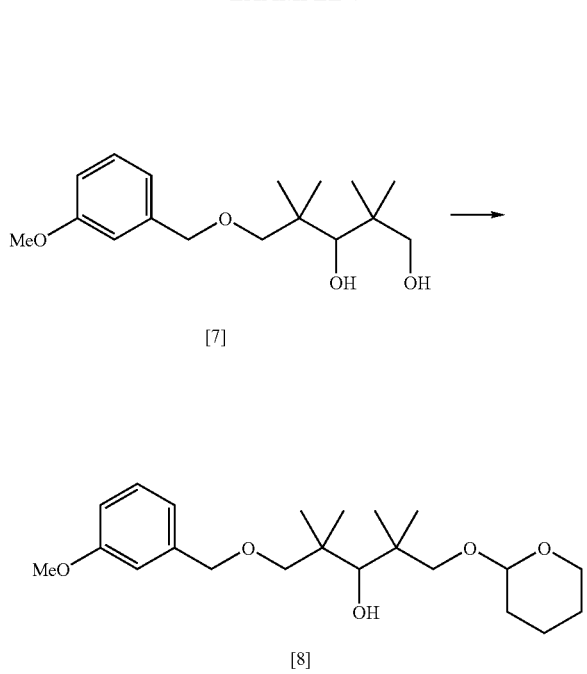

At room temperature, to a dichloromethane (20 mL) solution having 5-(3-methoxybenzyloxy)-2,2,4,4-tetramethylpentan-1,3-diol (compound (7)) (1.87 g, 6.326 mmol) dissolved, 3,4-dihydro-2H-pyran (0.7 mL, 7.672 mmol, 1.21 eq.) was added, and pyridinium p-toluene sulfonate (81.0 mg, 0.3223 mmol, 0.05 eq.) was added, followed by stirring for one day. The reaction solution was put into a saturated sodium hydrogencarbonate aqueous solution and extracted with ethyl acetate. The aqueous layer was again extracted with ethyl acetate, and the extract was put together with the previous organic layer, followed by washing with a saturated sodium chloride aqueous solution. The organic layer was dried over anhydrous magnesium sulfate and concentrated to obtain a residue as a yellow oil (2.53 g). This residue was subjected to silica gel column chromatography with a developing solvent (ethyl acetate:hexane=1:5). As a result, the desired 1-(3-methoxybenzyloxy)-2,2,4,4-tetramethyl-5-(tetrahydropyran-2-yloxy)pentan-3-ol (compound (8)) was obtained as a colorless oil (1.74 g, 4.564 mmol, 72.2%).

$^1$H-NMR (400 MHz, CDCl$_3$): δ$_H$ 1.02 (s, 1.5H), 1.04 (s, 1.5H), 1.04 (s, 1.5H), 1.05 (s, 1.5H), 1.06 (s, 1.5H), 1.09 (s, 1.5H), 1.10 (s, 1.5H), 1.11 (s, 1.5H), 1.53–1.82 (m, 6H), 3.14–3.70 (m, 9H) 3.81 (s, 3H), 3.81–3.86 (m, 1H), 4.48–4.58 (m, 3H), 6.81 (d with fine coupling, J=7.8 Hz, 1H), 6.90 (m, 2H), 7.25 (t, J=7.8 Hz, 1H) ppm $^{13}$C-NMR (125 MHz, CDCl$_3$): δ$_C$ 19.3, 19.6, 21.6, 21.9, 21.9, 22.0, 24.4, 24.7, 24.9, 25.0, 25.3, 25.4, 30.5, 30.6, 40.4, 40.5, 40.8, 55.1, 61.9, 62.4, 73.1, 77.7, 78.2, 80.4, 80.5, 80.6, 81.1, 99.0, 99.3, 112.7, 112.9, 113.0, 119.6, 129.3, 129.3, 140.1, 140.2, 169.6 ppm MASS (EI, 70 ev, m/z, %): 380 (M+, 3), 295 (29), 222 (13), 138 (60), 121 (100), 85 (97).

EXAMPLE 8

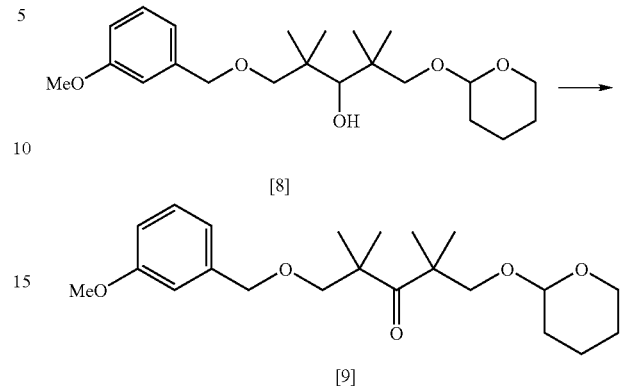

At room temperature, to a dichloromethane (15 mL) solution having pyridinium chlorochromate (1.31 g, 6.063 mmol, 1.58 eq.) and sellite (3.50 g) suspended, pyridine (0.46 mL, 6.335 mmol, 1.65 eq.) was added, and dichloromethane (5 mL) having 1-(3-methoxybenzyloxy)-2,2,4,4-tetramethyl-5-(tetrahydropyran-2-yloxy)pentan-3-ol (compound (8)) (1.46 g, 3.837 mmol) dissolved, was dropwise added over a period of 5 minutes, followed by stirring for 4 days. To this reaction solution, 2-propanol (4 mL) was added, followed by stirring for 30 minutes, and then, diethyl ether (100 mL) was added, followed by stirring for 30 minutes. The solution was subjected to sellite filtration, and the filtrate was concentrated to obtain a residue as a green oil (1.46 g). The residue was subjected to silica gel column chromatography with a developing solvent (ethyl acetate:hexane=1:7). As a result, the desired 1-(3-methoxybenzyloxy)-2,2,4,4-tetramethyl-5-(tetrahydropyran-2-yloxy)pentan-3-one (compound (9)) as a colorless oil (1.17 g, 3.099 mmol, 80.8%).

$^1$H-NMR (400 MHz, CDCl$_3$): δ$_H$ 1.23 (s, 3H), 1.28 (s, 3H), 1.28 (s, 3H), 1.32 (s, 3H), 1.46–1.70 (m, 6H), 3.46–3.83 (m, 6H), 3.80 (s, 3H), 4.47 (s, 2H), 4.55 (t, J=3.2 Hz, 1H), 6.80 (d with fine coupling, J=8.1 Hz, 1H), 6.86 (s, 1H), 6.87 (d, J=8.1 Hz, 1H), 7.23 (t, J=8.1 Hz, 1H) ppm $^{13}$C-NMR (100 MHz, CDCl$_3$): δ$_C$ 19.3, 23.3, 23.5, 23.6, 23.7, 25.5, 30.5, 50.1, 50.3, 55.1, 61.8, 63.0, 73.0, 76.0, 78.3, 98.9, 112.5, 112.9, 119.5, 129.1, 140.1, 159.5, 215.9 ppm IR (liquid film): 3441, 2990, 2954, 2873, 1164, 1010, 938 cm$^{-1}$ MASS (E1, 70 ev, m/z, %): 378 (M+, 3), 322 (4), 293 (21), 237 (2), 157 (16), 138 (11), 121 (91), 85 (100).

EXAMPLE 9

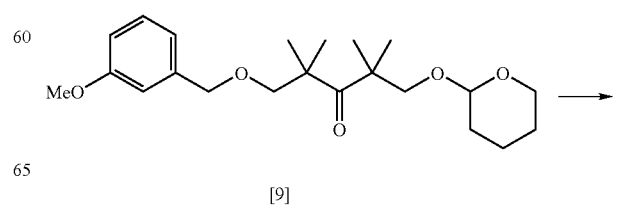

-continued

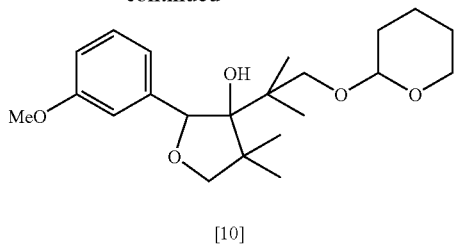

[10]

In a nitrogen atmosphere at room temperature, to a THF (40 mL) solution having diisopropylamine (6.5 mL, 46.38 mmol, 2.5 eq.) dissolved, a n-butyllithium hexane solution (1.61 M solution, 28 mL, 46.08 mmol, 2.4 eq.) was added, followed by stirring for 35 minutes. This reaction solution was cooled to −78° C., and a THF (30 mL) solution having 1-(3-methoxybenzyloxy)-2,2,4,4-tetramethyl-5-(tetrahydropyran-2-yloxy)pentan-3-one (compound (9)) (7.00 g, 18.50 mmol) dissolved, was dropwise added over a period of 30 minutes and stirred for two hours and 40 minutes. Water was added to this reaction solution for quenching. Then, this reaction solution was put into a saturated ammonium chloride aqueous solution and extracted with ethyl acetate. The aqueous layer was again extracted with ethyl acetate, and the extract was put together with the previous organic layer, followed by washing with a saturated sodium chloride aqueous solution. The organic layer was dried over anhydrous magnesium sulfate and concentrated to obtain a residue as a yellow oil (7.56 g). This residue was subjected to silica gel column chromatography with a developing solvent (ethyl acetate:hexane=1:4). As a result, the desired 3-hydroxy-2-(3-methoxybenzyloxy)-4,4-dimethyl-3-[1,1-dimethyl-2-(tetrahydropyran-2-yloxy)ethyl]tetrahydrofuran (compound (10)) was obtained as a colorless oil 10a (1.98 g, 5.230 mmol, 28.3%), 10a+10b (2.06 g, 5.436 mmol, 29.4%), 10b (2.59 g, 6.850 mmol, 37.0%), and the total (6.63 g, 17.62 mmol, 94.7%).

[10a]

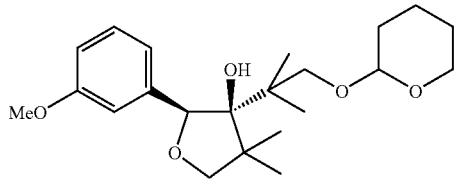

[10b]

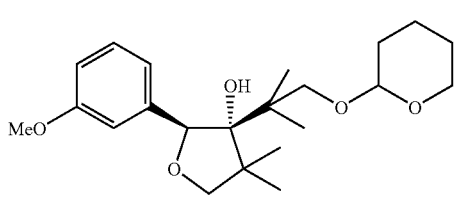

10a $^1$H-NMR (400 MHz, CDCl$_3$): δ$_H$ 1.03 (s, 3H), 1.29 (s, 3H), 1.35 (s, 3H), 1.57 (s, 3H), 1.54–1.79 (m, 6H), 2.70 (d, J=10.0 Hz, 1H), 3.45–3.48 (m, 1H), 3.76–3.80 (m, 2H), 3.80 (s, 3H). 3.87 (d, J=8.1 Hz, 1H), 4.13 (m, 1H), 4.88 (br, 1H), 5.14 (s, 1H), 6.80 (d with fine coupling, J=8.1 Hz, 1H), 7.11 (s, 1H), 7.12 (d, J=8.1 Hz, 1H), 7.20 (t, J=8.1 Hz, 1H) ppm.

$^{13}$C-NMR (100 MHz, CDCl$_3$): δ$_C$ 19.0, 25.3, 25.4, 30.3, 41.5, 47.9, 55.2, 62.0, 78.4, 80.0, 88.0, 90.7, 98.7, 112.7, 113.6, 120.3, 128.5, 142.0, 159.1 ppm IR (liquid film): 3455, 2940, 2874, 1722, 1603, 1487, 1390, 1281, 1037, 784 cm$^{-1}$ MASS (EI, 70 ev, m/z, %): 378 (M$^+$, 2), 276 (21), 157 (33), 136 (100), 126 (32), 107 (16), 85 (32), 55 (41).

10b $^1$H-NMR (400 MHz, CDCl$_3$): δ$_H$ 1.14 (s, 6H), 1.39 (s, 6H), 1.55–1.77 (m, 6H), 3.45–3.56 (m, 2H), 3.60 (d, J=8.0 Hz, 1H), 3.81 (s, 3H), 3.78–3.80 (m, 2H), 3.90 (d, J=8.0 Hz, 1H), 4.61 (s with fine coupling, 1H), 5.00 (s, 1H), 6.80 (d with fine coupling, J=7.3 Hz, 1H), 7.12–7.26 (m, 3H) ppm IR (liquid film): 3474, 2934, 1602, 1487, 1389, 1259, 1036, 779 cm$^{-1}$ MASS (EI, 70 ev, m/z, %): 378 (M$^+$, 5), 276 (17), 157 (72), 136 (100), 126 (31), 107 (14), 85 (54), 55 (36).

EXAMPLE 10

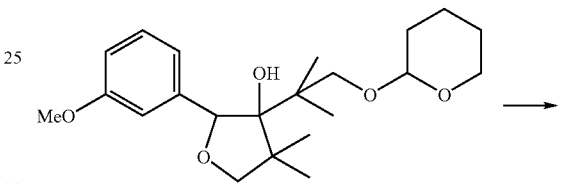

[10]

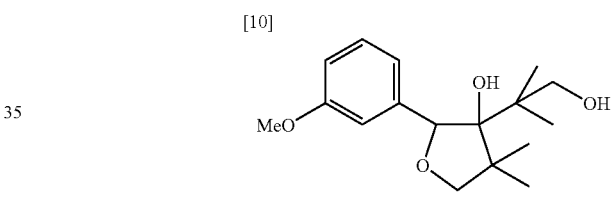

[11]

At room temperature, a methanol (10 mL) solution having 3-hydroxy-2-(3-methoxyphenyl)-4,4-dimethyl-3-[1,1-dimethyl-2-(tetrahydropyran-2-yloxy)ethyl]tetrahydrofuran (compound (10)) (1.05 g, 2.774 mmol) dissolved, a 1N hydrochloric acid aqueous solution (one drop) was added. Then, a 1N hydrochloric acid aqueous solution (one drop) was further added, followed by stirring for one day. This reaction solution was put into a saturated sodium hydrogencarbonate aqueous solution and extracted with ethyl acetate. The aqueous layer was again extracted with ethyl acetate, and the extract was put together with the previous organic layer, followed by washing with a saturated sodium chloride aqueous solution. The organic layer was dried over anhydrous magnesium sulfate and concentrated to obtain a residue as a yellow oil (827 mg). This residue was subjected to silica gel column chromatography with a developing solvent (ethyl acetate:hexane=1:2). As a result, the desired 3-(2-hydroxy-1,1-dimethyl)-2-(3-methoxyphenyl)-4,4-dimethyltetrahydrofuran-3-ol (compound (11)) was obtained as a colorless oil (766 mg, 2.602 mmol, 93.8%). Compound 11 was used for the subsequent reaction without purifying the isomers.

Colorless granular crystals (mp. 102.0 to 102.2° C.)

$^1$H-NMR (400 MHz, CDCl$_3$): δ$_H$ 0.79 (br-s, 3H), 1.01 (s, 3H), 1.25 (s, 3H), 1.37 (s, 3H), 2.17 (t, J=5.0 Hz, 1H), 3.22 (dd, J=10.9 and 5.0 Hz, 1H), 3.49–3.51 (m, 1H), 3.70 (d, J=8.1 Hz, 1H), 3.81 (s, 3H), 3.89 (d, J=8.1 Hz, 1H), 4.52 (br-s, 1H), 5.05 (s, 1H), 6.81 (d with fine coupling, J=8.0 Hz, 1H), 7.14 (s, 1H), 7.15 (d, J=8.0 Hz, 1H), 7.22 (t, J=8.0 Hz, 1H) ppm IR (KBr): 3295, 2938, 2877, 1607, 1583, 1486, 1456, 1284, 1043, 779 cm$^{-1}$ MASS (EI, 70 ev, m/z, %): 294 (M$^+$, 20), 276 (33), 236 (45), 136 (100), 121 (32), 107 (23), 85 (43), 73 (12), 70 (29).

EXAMPLE 11

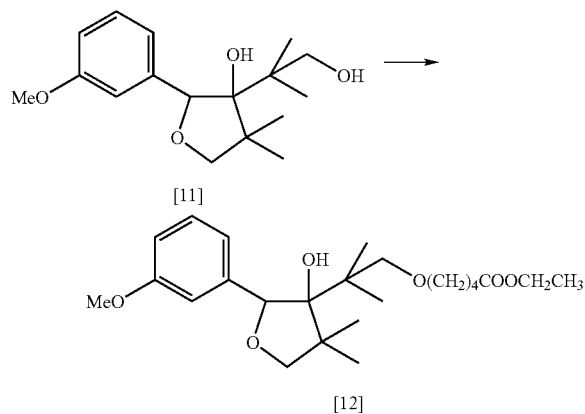

In a nitrogen atmosphere at 0° C., to a DMF (20 mL) solution having 60% sodium hydride (1.29 g, 32.25 mmol, 1.6 eq.) suspended, a DMF (40 mL) solution having 3-(2-hydroxy-1,1-dimethyl)-2-(3-methoxyphenyl)-4,4-dimethyltetrahydrofuran-3-ol (compound (11)) (6.00 g, 20.38 mmol) dissolved, was dropwise added over a period of 20 minutes, and 5-bromo valric acid (5 mL, 31.33 mmol, 1.5 eq.) was added, followed by stirring for 5 hours and 30 minutes. This reaction solution was put into a saturated ammonium chloride aqueous solution and extracted with ethyl acetate. The aqueous layer was again extracted with ethyl acetate, and the extract was put together with the previous organic layer, followed by washing with a saturated sodium chloride aqueous solution. The organic layer was dried over anhydrous magnesium sulfate and concentrated to obtain a residue as a yellow oil (10.5 g). This residue was subjected to silica gel column chromatography with a developing solvent (ethyl acetate:hexane=1:4). As a result, the desired 3-(7-ethoxycarbonyl-1,1-dimethyl-3-oxaheptyl)-3-hydroxy-2-(3-methoxyphenyl)-4,4-dimethyltetrahydrofuran (compound (12)) was obtained as a colorless oil 12a (6.03 g, 14.26 mmol, 70.0%), 12a+12b (1.68 g, 3.988 mmol, 19.6%), 12b (223 mg, 0.5285 mmol, 2.6%), and the total (7.93 g, 18.77 mmol, 92.1%).

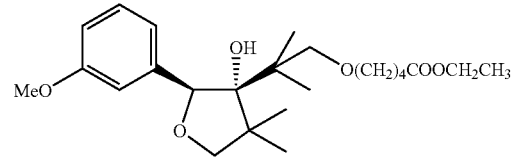

12a
$^1$H-NMR (400 MHz, CDCl$_3$): δ$_H$ 0.79 (br-s, 3H), 1.06 (s, 3H), 1.19 (s, 3H), 1.26 (t, J=7.1 Hz, 3H), 1.35 (s, 3H), 1.58–1.71 (m, 4H), 2.32 (t, J=7.1 Hz, 2H), 2.80 (d, J=9.3 Hz, 1H), 3.18–3.24 (br, 2H), 3.68 (d, J=8.1 Hz, 1H), 3.80 (s, 3H), 3.87 (d, J=8.1 Hz, 1H), 4.13 (q, J=7.1 Hz, 2H), 4.88 (br, 1H), 5.04 (s, 1H), 6.80 (d with fine coupling, J=8.1 Hz, 1H), 7.12 (s, 1H), 7.14 (d, J=8.1 Hz, 1H), 7.21 (t, J=8.1 Hz, 1H) ppm.
$^{13}$C-NMR (125 MHz, CDCl$_3$): δ$_C$ 14.1, 21.6, 23.3, 25.3, 28.8, 33.7, 41.5, 47.7, 55.0, 60.1, 70.6, 80.0, 81.7, 88.4, 92.3, 112.8, 114.0, 120.8, 128.4, 142.2, 159.0, 173.2 ppm IR (liquid film): 3447, 2936, 2873, 1734, 1603, 1488, 1372, 1093, 784 cm$^{-1}$ MASS (EI, 70 ev, m/z, %): 422 (M$^+$, 8), 245 (100), 243 (53), 188 (9), 147 (13), 136 (57), 107 (18) 101 (41), 83 (26), 55 (22).

12b
$^1$H-NMR (400 MHz, CDCl$_3$): δ$_H$ 1.01 (s, 3H), 1.16 (s, 3H), 1.21 (s, 3H), 1.25 (t, J=7.2 Hz, 3H), 1.37 (s, 3H), 1.32–1.37 (m, 2H), 1.49–1.52 (m, 2H), 2.23 (t, J=7.5 Hz, 2H), 2.55 (dd, J=13.5 and 6.5 Hz, 1H), 2.82 (d, J=9.3 Hz, 1H), 2.94 (dt, J=13.5 and 6.5 Hz, 1H), 3.08 (d. J=9.3 Hz, 1H), 3.44 (d, J=7.1 Hz, 1H), 3.81 (s, 3H), 4.12 (q, J=7.1 Hz, 2H), 4.12 (d, J=7.1 Hz, 1H), 6.83 (ddd, J=7.8 and 2.7 and 1.3 Hz, 1H), 7.10 (d with fine coupling, J=7.8 Hz, 1H), 7.16 (dd, J=2.7 and 1.3 Hz, 1H), 7.21 (t, J=7.8 Hz, 1H) ppm.
$^{13}$C-NMR (100 MHz, CDCl$_3$): δ$_C$ 14.3, 21.6, 23.7, 26.9, 28.7, 33.9, 40.4, 48.4, 55.2, 60.2, 70.5, 81.0, 81.7, 83.9, 86.4, 113.5, 115.5, 122.5, 128.3, 142.4, 159.0, 173.2 ppm IR (liquid film): 3403, 2963, 2873, 1734, 1599, 1486, 1372, 1094, 778 cm$^{-1}$ MASS (EI, 70 ev, m/z, %): 422 (M$^+$, 21), 245 (24), 243 (21), 147 (28), 136 (92), 107 (17), 101 (64), 55 (27).

EXAMPLE 12

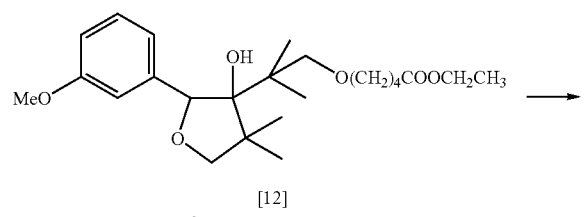

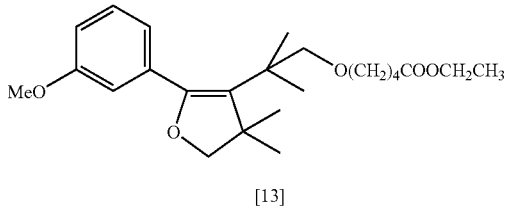

In a nitrogen atmosphere at 0° C., to a dichloromethane (14 mL) solution having 3-(7-ethoxycarbonyl-1,1-dimethyl-3-oxaheptyl)-3-hydroxy-2-(3-methoxyphenyl)-4,4-dimethyltetrahydrofuran (compound (12)) (1.39 g, 3.298 mmol) dissolved, pyridine (2.42 mL, 32.99 mmol, 10.0 eq.) was added, and thionyl chloride (0.3 mL, 4.113 mmol, 1.2 eq.) was added. The solution was gradually returned to room temperature, followed by stirring for 7 hours and 35 minutes. This reaction solution was put into a saturated sodium hydrogencarbonate aqueous solution and extracted with ethyl acetate. The aqueous layer was again extracted with ethyl acetate, and the extract was put together with the previous organic layer, followed by washing with a saturated sodium chloride aqueous solution. The organic layer was dried over anhydrous magnesium sulfate and concentrated to obtain a residue as a yellow oil (1.29 g). This residue was subjected to silica gel column chromatography with a developing solvent (ethyl acetate:hexane=1:6). As a result, the desired 4-(7-ethoxycarbonyl-1,1-dimethyl-3-oxaheptyl)-5-(3-methoxyphenyl)-3,3-dimethyl-2,3-dihydrofuran (compound (13)) was obtained as a colorless oil (1.04 g, 2.560 mmol, 77.6%).

$^1$H-NMR (400 MHz, CDCl$_3$): $\delta_H$ 1.04 (s, 6H), 1.25 (t, J=7.1 Hz, 3H), 1.31 (s, 6H), 1.54–1.57 (m, 2H), 1.66–1.70 (m, 2H), 2.32 (t, J=7.5 Hz, 2H), 3.10 (s, 1H), 3.25 (t, J=6.2 Hz, 2H), 3.80 (s, 3H), 3.87 (s, 2H), 3.80 (s, 3H), 3.87 (s, 2H), 4.12 (q, J=7.1 Hz, 2H), 6.85–6.86 (m, 2H), 6.90 (dt, J=7.4 and 1.2 Hz, 1H), 7.21–7.25 (m, 1H) ppm.

$^{13}$C-NMR (100 MHz, CDCl$_3$): $\delta_C$ 14.3, 21.9, 27.3, 27.4, 29.1, 34.1, 37.0, 47.0, 55.2, 60.1, 70.4, 79.5, 83.0, 113.9, 115.1, 122.3, 122.3, 128.7, 137.0, 151.0, 158.9, 173.5 ppm IR (liquid film): 2956, 2866, 1735, 1596, 1465, 1370, 1048, 785 cm$^{-1}$ MASS (EI, 70 ev, m/z %): 404 (M$^+$, 2), 258 (19), 245 (100), 243 (43), 135 (20), 55 (6).

EXAMPLE 13

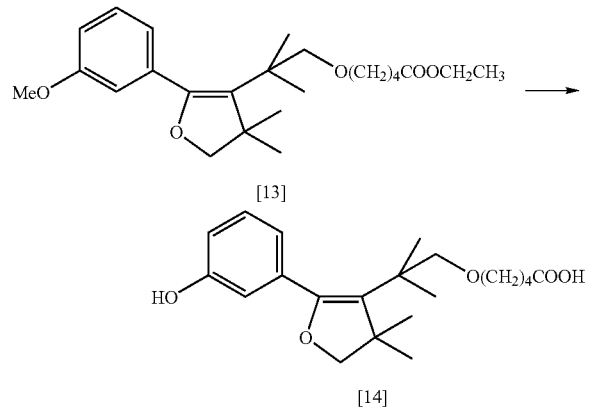

In a nitrogen atmosphere at 0° C., a DMF (4 mL) solution having 60% sodium hydride (465 mg, 11.63 mmol, 4.2 eq.) suspended, ethane thiol (1 mL, 13.60 mmol, 4.8 eq.) was added. The solution was returned to room temperature and then a DMF (7 mL) solution having 4-(7-ethoxycarbonyl-1,1-dimethyl-3-oxaheptyl)-5-(3-methoxyphenyl)-3,3-dimethyl-2,3-dihydrofuran (compound (13)) (1.13 g, 2.791 mmol) dissolved, was dropwise added over a period of 5 minutes, followed by refluxing for 11 hours. This reaction solution was put into a saturated ammonium chloride aqueous solution and extracted with ethyl acetate. The aqueous layer was again extracted with ethyl acetate, and the extract was put together with the previous organic layer, followed by a saturated sodium chloride aqueous solution. The organic layer was dried over anhydrous magnesium sulfate and concentrated to obtain a residue as a yellow oil (1.18 g). This residue was subjected to silica gel column chromatography with a developing solvent (ethyl acetate:hexane=1:1). As a result, the desired 4-(7-carboxy-1,1-dimethyl-3-oxaheptyl)-5-(3-hydroxyphenyl)-3,3-dimethyl-2,3-dihydrofuran (compound (14)) was obtained as a colorless oil (607 mg, 1.674 mmol, 60.0%).

$^1$H-NMR (400 MHz, CDCl$_3$): $\delta_H$ 1.03 (s, 6H), 1.30 (s, 6H), 1.56–1.63 (m, 2H), 1.70–1.77 (m, 2H), 2.42 (t, J=7.1 Hz, 2H), 3.10 (s, 2H), 3.26 (t, J=5.9 Hz, 2H), 3.86 (s, 2H), 6.79 (d with fine coupling, J=2.6 Hz, 1H), 6.86 (s, 1H), 6.85 (d, J=11.2 Hz, 1H), 7.17 (t, J=7.8 Hz, 1H) ppm.

$^{13}$C-NMR (100 MHz, CDCl$_3$): $\delta_C$ 21.9, 27.3, 27.5, 28.9, 33.7, 37.1, 47.0, 70.5, 79.5, 82.9, 115.3, 116.9, 122.0, 122.0, 128.9, 136.9, 150.7, 155.2, 178.8 ppm IR (liquid film): 3376, 2957, 2869, 1709, 1595, 1445, 1047, 787 cm$^{-1}$ MASS (EI, 70 ev, m/z, %): 362 (M$^+$, 3), 244 (22), 231 (100), 229 (46), 121 (37), 55 (10).

EXAMPLE 14

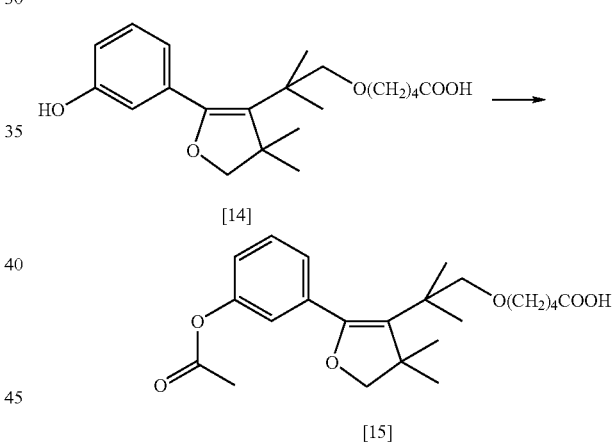

In a nitrogen atmosphere at room temperature, to a dichloromethane (20 mL) solution having 4-(7-carboxy-1,1-dimethyl-3-oxaheptyl)-5-(3-hydroxyphenyl)-3,3-dimethyl-2,3-dihydrofuran (compound (14)) (2.17 g, 6.000 mmol) dissolved, triethylamine (3 mL, 21.55 mmol, 3.6 eq.) was added. Further, the temperature was lowered to 0° C., and acetic anhydride (1 mL, 10.60 mmol, 1.8 eq.) was added. The solution was returned to room temperature and stirred for 8 hours and 10 minutes. This reaction solution was put into a saturated sodium chloride aqueous solution and extracted with ethyl acetate. The aqueous layer was again extracted with ethyl acetate, and the extract was put together with the previous organic layer, followed by washing with a saturated sodium chloride aqueous solution. The organic layer was dried over anhydrous magnesium sulfate and concentrated to obtain a residue as a yellow oil (2.66 g). This residue was subjected to silica gel column chromatography with a developing solvent (ethyl acetate:hexane=1:4). As a result, the desired 5-(3-acetoxyphenyl)-4-(7-carboxy- 1,1-dimethyl-3-oxaheptyl)-3,3-dimethyl-2,3-dihydrofuran (compound (15)) was obtained as a colorless oil (1.36 g, 3.335 mmol, 55.6%).

$^1$H-NMR (400 MHz, CDCl$_3$): δ$_H$ 1.05 (s, 6H), 1.30 (s, 6H), 1.54–1.61 (m, 2H), 1.67–1.74 (m, 2H), 2.28 (s, 3H), 2.38 (t, J=7.3 Hz, 2H), 3.08 (s, 2H), 3.24 (t, J=6.1 Hz, 2H), 3.86 (s, 2H), 7.05 (ddd, J=7.8 and 2.4 and 1.2 Hz, 1H), 7.08 (t, J=1.2 Hz, 1H), 7.19 (dt, J=7.8 and 1.2 Hz, 1H), 7.32 (t, J=7.8 Hz, 1H) ppm.

$^{13}$C-NMR (125 MHz, CDCl$_3$): δ$_C$ 21.1, 21.7, 27.3, 27.4, 28.9, 33.7, 37.0, 47.1, 70.3, 79.5, 83.1, 121.2, 123.0, 123.2, 127.3, 128.7, 137.2, 150.0, 150.1, 169.2, 179.2 ppm IR (liquid film): 2957, 2868, 1767, 1708, 1603, 1583, 1367, 1204, 785, 706 cm$^{-1}$ MASS (EI, 70 ev, m/z, %): 404 (M$^+$, 1), 273 (100), 271 (47), 229 (13), 163 (10), 121 (21).

EXAMPLE 15

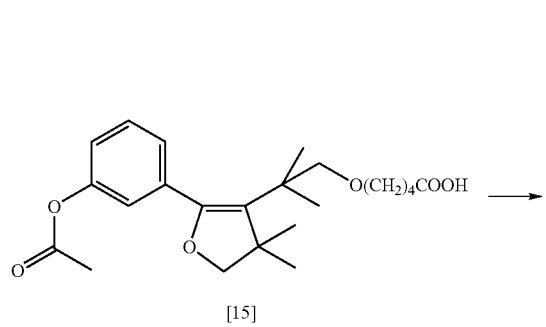

[15]

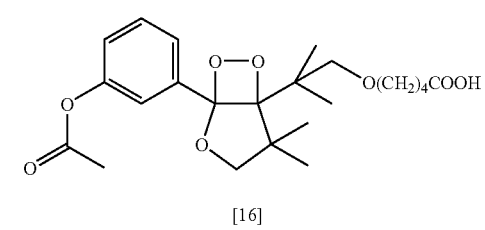

[16]

In an oxygen atmosphere at 0° C., to a dichloromethane solution having 5-(3-acetoxyphenyl-)-4-(7-carboxy-1,1-dimethyl-3-oxaheptyl)-3,3-dimethyl-2,3-dihydrofuran (compound (15)) (104 mg, 0.2666 mmol) dissolved, TPP (1.0 mg) was added, and the solution was irradiated by a 940 W sodium lamp for 30 minutes, stirred and concentrated to obtain a residue as a red oil (129 mg). This residue was subjected to silica gel column chromatography with a developing solvent (ethyl acetate:hexane=1:2). As a result, the desired 1-(3-acetoxyphenyl)-5-(7-carboxy-1,1-dimethyl-3-oxaheptyl)-4,4-dimethyl-2,6,7-trioxabicyclo[3.2.0]heptane (compound (16)) was obtained as a yellow oil (105 mg, 0.2412 mmol, 94.0%).

$^1$H-NMR (400 MHz, CDCl$_3$): δ$_H$ 0.87 (s, 3H), 1.14 (s, 3H), 1.15 (s, 3H), 1.38 (s, 3H), 1.54–1.58 (m, 2H), 1.63–1.68 (m, 2H), 2.30 (s, 3H), 2.35 (t, J=7.3 Hz, 2H), 3.24–3.32 (m, 4H), 3.82 (d, J=8.2 Hz, 1H), 4.58 (d, J=8.2 Hz, 1H), 7.14 (d with fine coupling, J=8.0 Hz, 1H), 7.36 (s with fine coupling, 1H), 7.41 (t, J=8.0 Hz, 1H), 7.51 (d, J=8.0 Hz, 1H), 9.79 (br, 1H) ppm.

$^{13}$C-NMR (125 MHz, CDCl$_3$): δ$_C$ 17.7, 20.6, 21.1, 21.5, 22.2, 24.8, 28.8, 33.6, 41.1, 45.6, 70.5, 75.9, 80.3, 105.0, 116.4, 122.0, 122.7, 125.7, 128.9, 137.4, 150.3, 169.1, 179.5 ppm IR (liquid film): 2956, 1767, 1709, 1487, 1370, 1206, 793, 700 cm$^{-1}$ MASS (EI, 70 ev, m/z, %): 404 (M$^+$, 1), 273 (18), 163 (91), 121 (54), 101 (100), 83 (30).

EXAMPLE 16

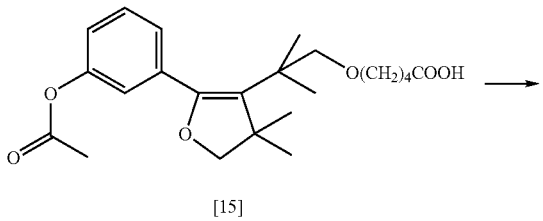

[15]

[17]

In a nitrogen atmosphere at room temperature, to a THF (2.5 mL) solution having 5-(3-acetoxyphenyl)-4-(7-carboxy-1,1-dimethyl-3-oxaheptyl)-3,3-dimethyl-2,3-dihydrofuran (compound (15)) (209 mg, 0.5167 mmol) dissolved, ethanol (48 mg, 1.042 mmol, 2.0 eq.) and triphenyl phosphine (275 mg, 1.048 mmol, 2.0 eq.) were added, and further diethyl azodicarboxylate (185 mg, 1.062 mmol, 2.1 eq.) dissolved in THF (0.5 mL) was added, followed by stirring for 20 minutes. This reaction solution was put into a 1N hydrochloric aqueous solution and a saturated sodium chloride aqueous solution, and extracted with ethyl acetate. The aqueous layer was again extracted with ethyl acetate, and the extract was put together with the previous organic layer, followed by washing with a saturated sodium hydrogencarbonate aqueous solution and a saturated sodium chloride aqueous solution. The organic layer was dried over anhydrous magnesium sulfate and concentrated to obtain a residue. This residue was subjected to silica gel column chromatography with a developing solvent (ethyl acetate: hexane=1:20). As a result, the desired 5-(3-acetoxyphenyl)-4-(7-ethoxycarbonyl-1,1-dimethyl-3-oxaheptyl)-3,3-dimethyl-2,3-dihydrofuran (compound (17)) was obtained as a colorless oil (172 mg, 0.3976 mmol, 77.0%).

$^1$H-NMR (400 MHz, CDCl$_3$): δ$_H$ 1.04 (s, 6H), 1.25 (t, J=7.1 Hz, 3H), 1.30 (s, 6H), 1.53–1.58 (m, 2H), 1.64–1.70 (m, 2H), 2.78 (s, 3H), 2.32 (t, J=7.4 Hz, 2H), 3.07 (s, 2H), 3.23 (t, J=6.4 Hz, 2H), 3.86 (s, 2H), 4.12 (q, J=7.2 Hz, 2H), 7.05 (ddd, J=7.9 and 2.5 and 1.2 Hz, 1H), 7.08 (t, J=1.2 Hz, 1H), 7.18 (td, J=7.9 and 1.2 Hz, 1H), 7.32 (t, J=7.9 Hz, 1H) ppm.

$^{13}$C-NMR (125 MHz, CDCl$_3$): δ$_C$ 14.2, 21.0, 21.9, 27.2, 27.3, 29.0, 34.1, 37.0, 47.1, 60.1, 70.4, 79.4, 83.0, 121.2, 123.0, 123.2, 127.2, 128.6, 137.2, 150.0, 169.0, 173.6 ppm IR (liquid film): 2957, 2867, 1768, 1735, 1203 cm$^{-1}$ MASS (EI, 70 ev, m/z, %): 432 (M$^+$, 1), 286 (33), 273 (100), 229 (14), 163 (5), 149 (37), 129 (8), 121 (14), 101 (8).

EXAMPLE 17

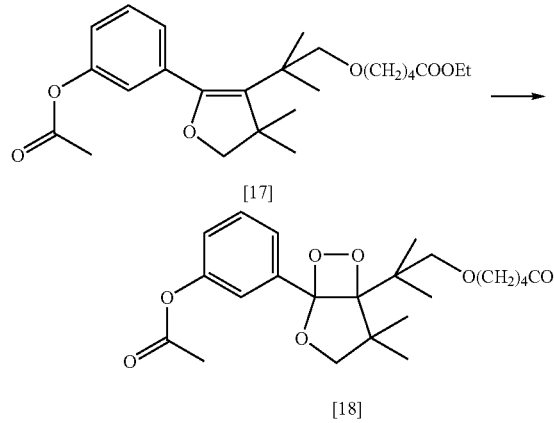

In an oxygen atmosphere at 0° C., to a dichloromethane (7 mL) solution having 5-(3-acetoxyphenyl)-4-(7-ethoxycarbonyl-1,1-dimethyl-3-oxaheptyl)-3,3-dimethyl-2,3-dihydrofuran (compound (17)) (76 mg, 0.1750 mmol) dissolved, TPP (0.8 mg) was added, and the solution was irradiated by a 940 W sodium lamp for 45 minutes, stirred and concentrated to obtain a residue as a yellow oil. This residue was subjected to silica gel column chromatography with a developing solvent (ethyl acetate:hexane=1:10). As a result, the desired 1-(3-acetoxyphenyl)-5-(7-ethoxycarbonyl-1,1-dimethyl-3-oxaheptyl)-4,4-dimethyl-2,6,7-trioxabicyclo[3.2.0]heptane (compound (18)) was obtained as a yellow oil (78 mg, 0.1679 mmol, 95.9%).

$^1$H-NMR (400 MHz, CDCl$_3$): $\delta_H$ 0.86 (s, 3H), 1.15 (s, 3H), 1.16 (s, 3H), 1.25 (t, J=7.1 Hz, 3H), 1.38 (s, 3H), 1.52–1.55 (m, 2H), 1.61–1.66 (m, 2H), 2.29 (t, J=7.7 Hz, 2H), 2.30 (s, 3H), 3.25 (dd, J=9.3 and 7.7 Hz, 2H), 3.29 (t, J=6.2 Hz, 2H), 3.82 (d, J=8.2 Hz, 1H), 4.12 (q, J=7.1 Hz, 2H), 4.58 (d, J=8.2 Hz, 1H), 7.14 (d with fine coupling, J=8.0 Hz, 1H), 7.37 (s with fine coupling, 1H), 7.41 (t, J=8.0 Hz, 1H), 7.51 (d, J=8.0 Hz, 1H) ppm.

$^{13}$C-NMR (125 MHz, CDCl$_3$): $\delta_C$ 14.2, 21.1, 21.8, 22.3, 28.9, 34.0, 41.1, 45.6, 60.2, 70.6, 75.9, 80.3, 105.0, 116.4, 121.9, 122.7, 125.7, 128.9, 137.5, 150.4, 169.1, 173.6 ppm IR (liquid film): 2979, 1767, 1733, 1487, 1370, 1205, 701 cm$^{-1}$ MASS (EI, 70 ev, m/z, %): 432 (M$^+$, trace), 319 (15), 263 (35), 229 (20), 163 (91), 154 (trace), 149 (10), 129 (100), 121 (33), 101 (36).

EXAMPLE 18

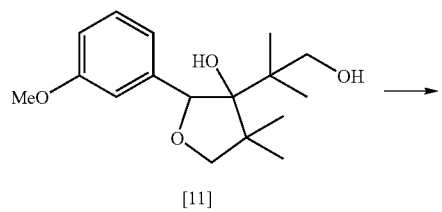

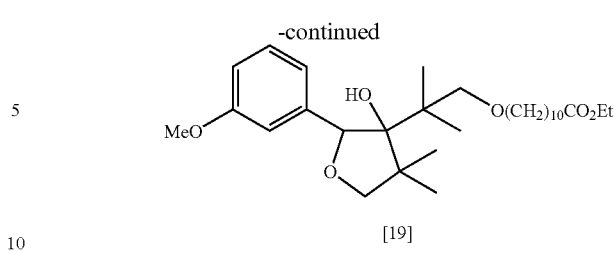

To a solution having sodium hydride (60% in mineral oil, 412 mg, 10.3 mmol) suspended in anhydrous DMF (7 mL) in a nitrogen stream at 0° C., 3-hydroxy-3-(2-hydroxy-1,1-dimethylethyl)-2-(3-methoxyphenyl)-4,4-dimethyltetrahydrofuran (compound (11)) (1.51 g, 5.13 mmol) dissolved in anhydrous DMF (4 mL), was dropwise added, followed by stirring at 0° C. for 30 minutes and at room temperature for 20 minutes. To this solution, ethyl 11-iodoundecanoate (3.51 g, 10.3 mmol) dissolved in anhydrous DMF (3 mL) was added at 0° C., followed by stirring for 4 hours and then by stirring at room temperature overnight. The reaction mixture was put into a saturated ammonium chloride aqueous solution and extracted with ethyl acetate. The organic layer was washed with a saturated sodium chloride aqueous solution, dried over anhydrous magnesium sulfate and then concentrated. The concentrate was put into a silica gel column and developed with a mixed solvent of hexane and ethyl acetate (4:1), whereby 3-(13-ethoxycarbonyl-1,1-dimethyl-3-oxatridecan-1-yl)-2-(3-methoxyphenyl-4,4-dimethyltetrahydrofuran (compound (19)) was obtained as a colorless oil in an amount of 2.52 g in a yield of 97.0%.

$^1$H-NMR (400 Hz, CDCl$_3$) $\delta_H$ 0.78 (s, 3H), 1.01 (s, 3H), 1.20–1.45 (m, 21H), 1.57–1.67 (m, 2H), 1.77–1.87 (m, 2H), 2.29 (t, J=7.6 Hz, 2H), 3.19 (t, J=7.1 Hz, 2H), 3.42–3.65 (m, 1H), 3.70 (d, J=8.1 Hz, 1H), 3.81 (s, 3H), 3.89 (d, J=8.1 Hz, 1H), 4.12 (q, J=7.2 Hz, 2H), 4.50–4.70 (m, 1H), 5.04 (s, 1H), 6.81 (d with fine coupling, J=7.8 Hz, 1H), 7.12–7.17 (m, 2H), 7.22 (t, J=7.8 Hz, 1H) ppm.

EXAMPLE 19

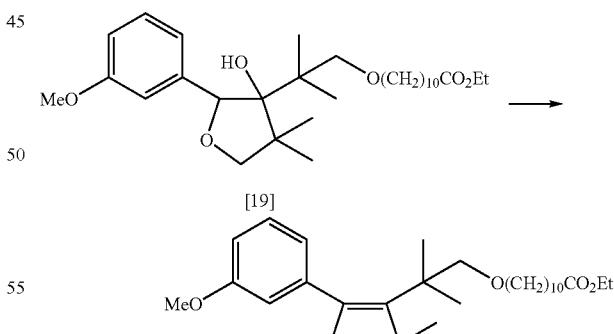

To a solution having 3-(13-ethoxycarbonyl-1,1-dimethyl-3-oxatridecan-1-yl)-2-(3-methoxyphenyl-4,4-dimethyltetrahydrofuran (compound (19)) (1.21 g, 2.39 mmol) and pyridine (2.0 mL, 24.7 mmol) dissolved in anhydrous dichloromethane (12 mL) in a nitrogen stream and stirred at 0° C., thionyl chloride (0.25 mL, 3.43 mmol) was added, followed by stirring for 5 minutes and then by stirring at room temperature for one hour. The reaction mixture was put into a sodium hydrogencarbonate aqueous solution and extracted with ethyl acetate. The organic layer was washed with a saturated sodium chloride aqueous solution, dried over anhydrous magnesium sulfate and then concentrated. The concentrate was put into a silica gel column and developed with a mixed solvent of hexane and ethyl acetate (10:1), whereby 4-(13-ethoxycarbonyl-1,1-dimethyl-3-oxatridecan-1-yl)-5-(3-methoxyphenyl-3,3-dimethyl-2,3-dihydrofuran (compound (20)) was obtained as a colorless oil in an amount of 1.06 g in a yield of 90.8%.

$^1$H-NMR (400 Hz, CDCl$_3$) δ$_H$ 1.04 (s, 6H), 1.23–1.34 (m, 21H), 1.46–1.55 (m, 2H) 1.57–1.65 (m, 2H), 2.28 (t, J=7.6 Hz, 2H) 3.11 (s, 2H), 3.24 (t, J=6.6 Hz, 2H), 3.80 (s, 3H), 3.87 (s, 2H), 4.12 (q, J=7.1 Hz, 2H). 6.83–6.88 (m, 2H), 6.91 (d with fine coupling, J=7.5 Hz, 1H), 7.22 (t with fine coupling, J=7.5 Hz, 1H) ppm.

EXAMPLE 20

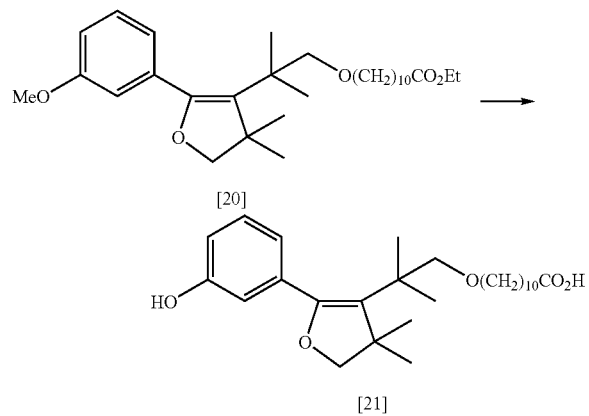

To a solution having sodium hydride (60% in mineral oil, 704 mg, 17.6 mmol) suspended in anhydrous DMF (30 mL) in a nitrogen stream at 0° C., ethanethiol (1.5 mL, 20.3 mmol) was dropwise added, followed by stirring at room temperature for a few minutes. This solution was added to 4-(13-ethoxycarbonyl-1,1-dimethyl-3-oxatridecan-1-yl)-5-(3-methoxyphenyl-3,3-dimethyl-2,3-dihydrofuran (compound (20)) in a nitrogen stream, followed by heating and stirring at 140° C. for 20 minutes and then at 150° C. for one hour. The reaction mixture was put into dilute hydrochloric acid and extracted with ethyl acetate. The organic layer was washed with a saturated sodium chloride aqueous solution, dried over anhydrous magnesium sulfate and then concentrated. The concentrate was put into a silica gel column and developed with a mixed solvent of hexane and ethyl acetate (2:1), whereby 4-(13-carboxy-1,1-dimethyl-3-oxatridecan-1-yl)-5-(3-hydroxyphenyl)-3,3-dimethyl-2,3-dihydrofuran (compound (21)) was obtained as a colorless oil in an amount of 1.579 g in a yield of 94.2%.

$^1$H-NMR (400 Hz, CDCl$_3$) δ$_H$ 1.04 (s, 6H), 1.20–1.40 (m, 18H), 1.46–1.55 (m, 2H), 1.58–1.68 (m, 2H), 2.35 (t, J=7.4 Hz, 2H), 3.12 (s, 2H), 3.25 (t, J=6.6 Hz, 2H), 3.86 (s, 2H), 6.76 (d with fine coupling, J=8.0 Hz, 1H), 6.79 (s with fine coupling, 1H), 6.88 (d, 1H), 7.17 (dd, J=8.0 and 7.6 Hz, 1H) ppm.

EXAMPLE 21

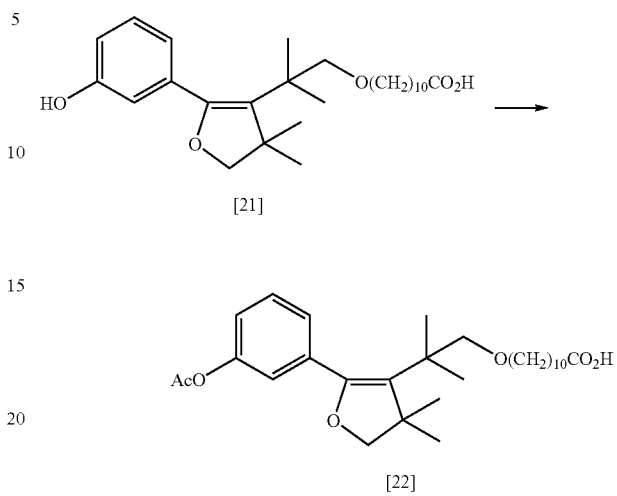

To a solution having 4-(13-carboxy-1,1-dimethyl-3-oxatridecan-1-yl)-5-(3-hydroxyphenyl)-3,3-dimethyl-2,3-dihydrofuran (compound (21)) (1.57 g, 3.52 mmol) and triethylamine (2.5 mL, 17.9 mmol) dissolved in anhydrous dichloromethane (15 mL) and stirred in a nitrogen atmosphere at 0° C., acetic anhydride (0.50 mL, 5.30 mmol) was added, followed by stirring for 1.5 hours. The reaction mixture was put into dilute hydrochloric acid and extracted with ethyl acetate. The organic layer was washed with a saturated sodium chloride aqueous solution, dried over anhydrous magnesium sulfate and then concentrated. The concentrate was put into a silica gel column and developed with a mixed solvent of hexane and ethyl acetate (2:1), whereby 5-(3-acetoxyphenyl)-4-(13-carboxy-1,1-dimethyl-3-oxatridecan-1-yl)-3,3-dimethyl-2,3-dihydrofuran anhydride was obtained as a colorless oil in an amount of 1.353 g in a yield of 80.2%. Then, 5-(3-acetoxyphenyl)-4-(13-carboxy-1,1-dimethyl-3-oxatridecan-1-yl)-3,3-dimethyl-2,3-dihydrofuran (compound (22)) was obtained in an amount of 126 mg in a yield of 7.3%.

$^1$H-NMR (400 Hz, CDCl$_3$) δ$_H$ 1.03 (s, 6H), 1.20–1.37 (m, 18H), 1.46–1.55 (m, 2H), 1.57–1.67 (m, 2H), 2.27 (s, 3H), 2.34 (t, J=7.5 Hz, 2H), 3.09 (s, 2H), 3.23 (t, J=6.5 Hz, 2H), 3.86 (s, 2H), 7.05 (ddd, J=8.1 and 2.4 and 1.1 Hz, 1H), 7.09 (s with fine coupling, 1H), 7.20 (d with fine coupling, J=7.7 Hz, 1H), 7.31 (dd, J=8.1 and 7.7 Hz, 1H) ppm.

EXAMPLE 22

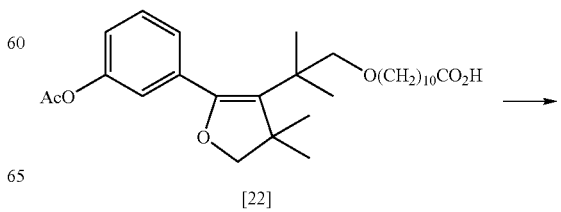

-continued

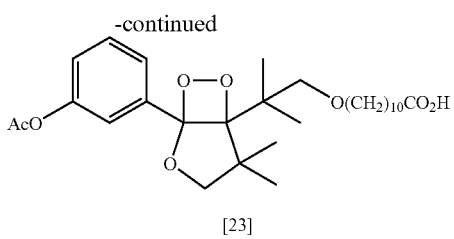

[23]

5-(3-acetoxyphenyl)-4-(13-carboxy-1,1-dimethyl-3-oxatridecan-1-yl)-3,3-dimethyl-2,3-dihydrofuran (compound (22)) (125 mg, 0.256 mmol) and TPP (1 mg) were added to dichloromethane (12 mL), and the mixture was irradiated with visible light by a 940 W sodium lamp in an oxygen atmosphere at 0° C. for 30 minutes. The reaction mixture was concentrated, and the concentrate was put into a silica gel column and developed with a mixed solvent of hexane and ethyl acetate (10:1 to 5:1), whereby 1-(3-acetoxyphenyl)-5-(13-carboxy-1,1-dimethyl-3-oxatridecan-1-yl)-4,4-dimethyl-2,6,7-trioxabicyclo[3.2.0]heptane (compound (23)) was obtained in an amount of 133 mg in a yield of 97.6%.

$^1$H-NMR (400 Hz, CDCl$_3$) $\delta_H$ 0.86 (s, 3H), 1.15 (s, 3H), 1.16 (s, 3H), 1.20–1.40 (m, 12H), 1.39 (s, 3H), 1.43–1.52 (m, 2H), 1.58–1.67 (m, 2H), 2.30 (s, 3H), 2.35 (t, J=7.5 Hz, 2H), 3.23 (s, 2H), 3.27 (t with fine coupling, J=6.6 Hz, 2H) 3.82 (d, J=8.1 Hz, 1H), 4.58 (d, J=8.1 Hz, 1H), 7.14 (ddd, J=8.1 and 2.3 and 1.1 Hz, 1H), 7.37 (s with fine coupling, 1H), 7.40 (dd, J=8.1 and 7.9 Hz, 1H), 7.51 (d, J=7.9 Hz, 1H) ppm.

EXAMPLE 23

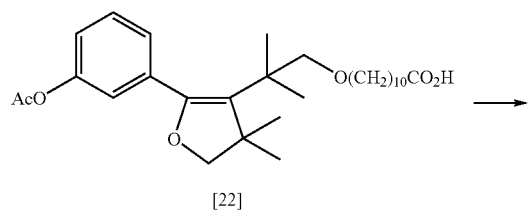

[22]

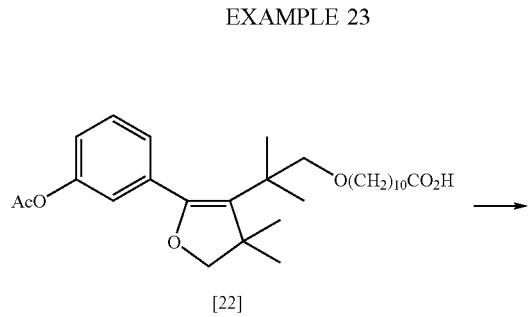

[24]

To a solution having ethanol (34 mg, 0.74 mmol), triphenyl phosphine (204 mg, 0.78 mmol) and 5-(3-acetoxyphenyl)-4-(13-carboxy-1,1-dimethyl-3-oxatridecan-1-yl)-3,3-dimethyl-2,3-dihydrofuran (compound (22)) (126 mg, 0.258 mmol) dissolved in anhydrous THF (1.0 mL) in a nitrogen stream at room temperature and stirred, diethyl azodicarboxylate (135 mg, 0.77 mmol) dissolved in anhydrous THF (0.5 mL), was added, followed by stirring for 20 minutes. After completion of the reaction, the reaction mixture was put into dilute hydrochloric acid and extracted with ethyl acetate. The organic layer was washed with a saturated sodium chloride aqueous solution, dried over anhydrous magnesium sulfate and then concentrated. The concentrate was put into a silica gel column and developed with a mixed solvent of hexane and ethyl acetate (20:1 to 10:1), whereby 5-(3-acetoxyphenyl)-4-(13-ethoxycarbonyl-1,1-dimethyl-3-oxatridecan-1-yl)-3,3-dimethyl-2,3-dihydrofuran (compound (24)) was obtained as a colorless oil in an amount of 111 mg in a yield of 83.3%.

$^1$H-NMR (500 Hz, CDCl$_3$) $\delta_H$ 1.03 (s, 6H), 1.23–1.34 (m, 21H), 1.47–1.54 (m, 2H), 1.57–1.65 (m, 2H), 2.28 (s, 3H), 2.28 (t, J=7.6 Hz, 2H), 3.08 (s, 2H), 3.22 (t, J=6.5 Hz, 2H), 3.86 (s, 2H), 4.12 (q, J=7.1 Hz, 1H), 7.05 (ddd, J=8.0 and 2.4 and 1.0 Hz, 1H), 7.09 (s with fine coupling, 1H), 7.20 (d with fine coupling, J=7.6 Hz, 1H), 7.32 (dd, J=8.0 and 7.6 Hz, 1H) ppm.

EXAMPLE 24

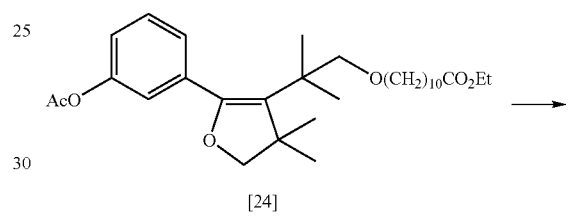

[24]

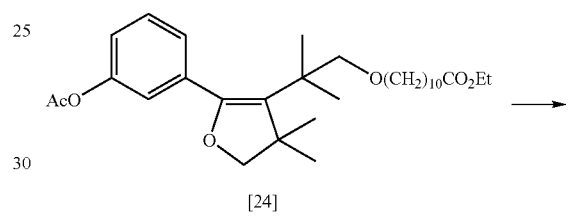

[25]

5-(3-acetoxyphenyl)-4-(13-ethoxycarbonyl-1,1-dimethyl-3-oxatridecan-1-yl)-3,3-dimethyl-2,3-dihydrofuran (compound (24)) (57.8 mg, 0.112 mmol) and TPP (0.6 mg) were added to dichloromethane (6 mL), and the mixture was irradiated with visible light by a 940 W sodium lamp in an oxygen atmosphere at 0° C. for 30 minutes. The reaction mixture was concentrated, and the concentrate was put into a silica gel column and developed with a mixed solvent of hexane and ethyl acetate (10:1 to 5:1), whereby 1-(3-acetoxyphenyl)-5-(13-ethoxycarbonyl-1,1-dimethyl-3-oxatridecan-1-yl)-4,4-dimethyl-2,6,7-trioxabicyclo[3.2.0]heptane (compound (25)) was obtained as a colorless oil in an amount of 46 mg in a yield of 75.0%.

$^1$H-NMR (400 Hz, CDCl$_3$) $\delta_H$ 0.86 (s, 3H), 1.15 (s, 3H), 1.16 (s, 3H), 1.22–1.38 (m, 15H), 1.39 (s, 3H), 1.44–1.52 (m, 2H), 1.57–1.65 (m, 2H), 2.28 (t, J=7.6 Hz, 2H), 2.30 (s, 3H), 3.23 (s, 2H), 3.26 (t with fine coupling, J=6.6 Hz, 2H), 3.82 (d, J=8.1 Hz, 1H), 4.12 (q, J=7.2 Hz, 2H), 4.58 (d, J=8.1 Hz, 1H), 7.14 (d with fine coupling, J=7.6 Hz, 1H), 7.37 (s with fine coupling, 1H), 7.41 (dd, J=8.0 and 7.8 Hz, 1H), 7.52 (d, J=7.8 Hz, 1H) ppm.

EXAMPLE 25

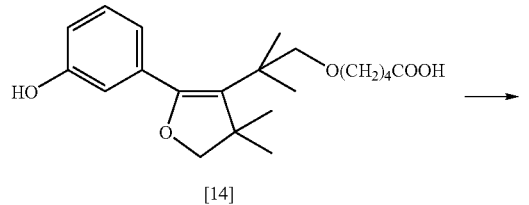

[14]

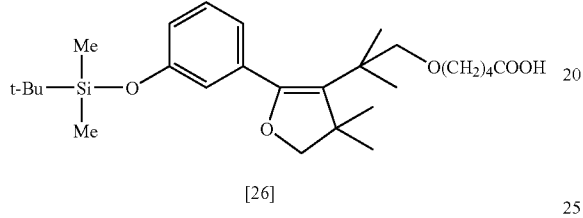

[26]

In a nitrogen atmosphere at 0° C., to a DMF (10 mL) solution having 4-(7-carboxy-1,1-dimethyl-3-oxaheptyl)-5-(3-hydroxyphenyl)-3,3-dimethyl-2,3-dihydrofuran (compound (14)) (500 mg, 1.379 mmol) dissolved, imidazole (282 mg, 4.142 mmol, 3.0 eq.) was added, and further, t-butyldimethylchlorosilane (624 mg, 4.140 mmol, 3.0 eq.) was added. The solution was returned to room temperature and stirred for two hours. This reaction solution was put into a saturated sodium chloride aqueous solution and extracted with ethyl acetate. The aqueous layer was again extracted with ethyl acetate, and the extract was put together with the previous organic layer, followed by washing with a saturated sodium chloride aqueous solution. The organic layer was dried over anhydrous magnesium sulfate and concentrated to obtain a residue as a yellow oil (806 mg). The residue was dissolved in methanol (15 mL) and cooled to 0° C. Water (5 mL) having potassium carbonate (380 mg, 2.749 mmol) dissolved therein, was dropwise added thereto, followed by stirring for 30 minutes. This reaction solution was put into a saturated sodium chloride aqueous solution and extracted with ethyl acetate. The aqueous layer was again extracted with ethyl acetate, and the extract was put together with the previous organic layer, followed by washing with a saturated sodium chloride aqueous solution. The organic layer was dried over anhydrous magnesium sulfate and concentrated to obtain a residue as a yellow oil. The residue was subjected to silica gel column chromatography with a developing solvent (ethyl acetate:hexane=1:1). As a result, the desired 4-(7-carboxy-1,1-dimethyl-3-oxaheptyl)-5-(3-t-butyldimethylsiloxyphenyl)-3,3-dimethyl-2,3-dihydrofuran (compound (26)) was obtained as a colorless oil (475 mg, 0.997 mmol, 72.3%).

$^1$H-NMR (500 MHz, CDCl$_3$): $\delta_H$ 0.18 (s, 6H), 0.98 (s, 9H), 1.04 (s, 6H), 1.31 (s, 6H), 1.56–1.62 (m, 2H), 1.67–1.76 (m, 2H), 2.38 (t, J=7.0Hz, 2H), 3.10 (s, 2H), 3.25 (t, J=6.5 Hz, 2H), 3.87 (s, 2H), 6.77–6.80 (m, 2H), 6.90 (dd, J=8.0 and 1.5 Hz, 1H), 7.15–7.19 (m, 1H) ppm.

EXAMPLE 26

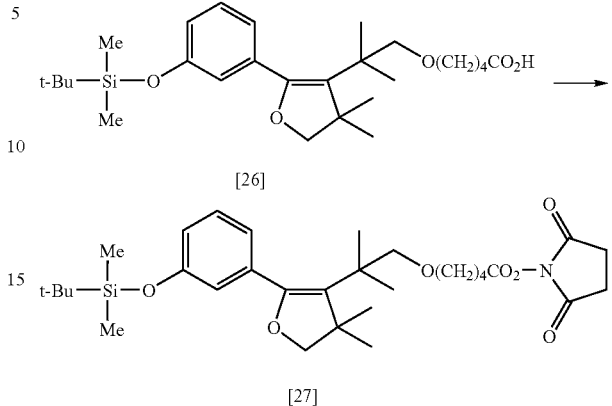

[26]

[27]

To a solution having 5-(3-t-butyldimethylsiloxyphenyl)-4-(7-carboxy-1,1-dimethyl-3-oxaheptyl)-3,3-dimethyl-2,3-dihydrofuran (compound (26)) (394 mg, 0.827 mmol) dissolved in anhydrous acetonitrile (5 mL) in a nitrogen atmosphere at room temperature, di(N-succinimidyl)carbonate (318 mg, 1.241 mmol) and triethylamine (one drop) were added, followed by stirring for 50 minutes. The reaction solution was concentrated, and the concentrate was put into a silica gel column and developed with a mixed solvent of hexane and ethyl acetate (1:1), whereby 5-(3-t-butyldimethylsiloxyphenyl)-3,3-dimethyl-4-(1,1-dimethyl-7-succinimidoxycarbonyl-3-oxaheptyl)-2,3-dihydrofuran (compound (27)) was obtained as a colorless oil in an amount of 433 mg in a yield of 91.2%.

$^1$H-NMR (500 MHz, CDCl$_3$): $\delta_H$ 0.18 (s, 6H), 0.98 (s, 9H), 1.04 (s, 6H), 1.31 (s, 6H), 1.61–1.67 (m, 2H), 1.81 (quintet, J=7.5 Hz, 2H), 2.64 (t, J=7.5 Hz, 2H), 2.84 (br-d, J=6.5 Hz, 4H), 3.10 (s, 2H), 3.26 (t, J=6.0 Hz, 2H), 3.86 (s, 2H), 6.77–6.80 (m, 2H), 6.90 (dd, J=9.0 and 1.5 Hz, 1H), 7.17 (t, J=8.0 Hz, 1H) ppm.

EXAMPLE 27

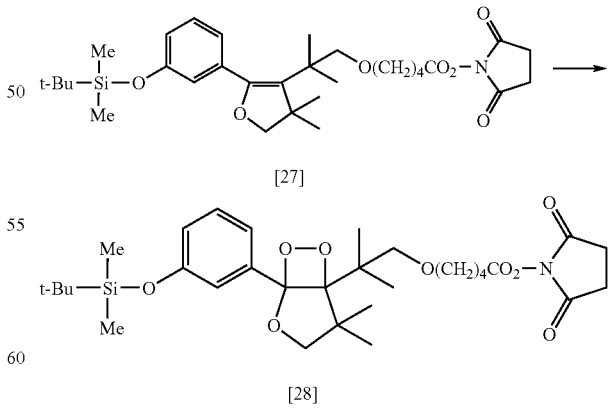

[27]

[28]

5-(3-t-butyldimethylsiloxyphenyl)-3,3-dimethyl-4-(1,1-dimethyl-7-succinimidoxycarbonyl-3-oxaheptyl)-2,3-dihydrofuran (compound (27)) (313 mg, 0.545 mmol) and TPP (2.5 mg) were added to dichloromethane (15 mL), and the mixture was irradiated with visible light by a 940 W sodium lamp in an oxygen atmosphere at 0° C. for one hour. The reaction mixture was concentrated, and the concentrate was put into a silica gel column and developed with a mixed solvent of hexane and ethyl acetate (1:1), whereby 1-(3-t-butyldimethylsiloxyphenyl)-4,4-dimethyl-5-(1,1-dimethyl-7-succinimidoxycarbonyl-3-oxaheptyl)-2,6,7-trioxabicyclo[3.2.0]heptane (compound (28)) was obtained in an amount of 276 mg in a yield of 83.6%.

1H-NMR (500 MHz, CDCl$_3$): $\delta_H$ 0.19 (s, 6H), 0.86 (s, 3H), 0.98 (s, 9H), 1.14 (s, 3H), 1.17 (s, 3H), 1.38 (s, 3H), 1.60–1.66 (m, 2H), 1.78 (quintet, J=8.0 Hz, 2H), 2.62 (t, J=7.0 Hz, 2H), 2.84 (br-d, J=6.0 Hz, 4H), 3.24 (d, J=9.0 Hz, 1H), 3.30–3.35 (m, 3H), 3.81 (d, J=8.5 Hz, 1H), 4.57 (d, J=8.5 Hz, 1H), 6.85–6.88 (m, 1H), 7.11 (s, 1H), 7.20–7.27 (m, 2H) ppm.

EXAMPLE 28

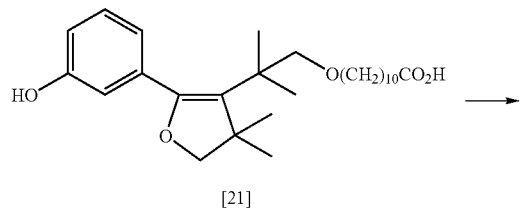

[21]

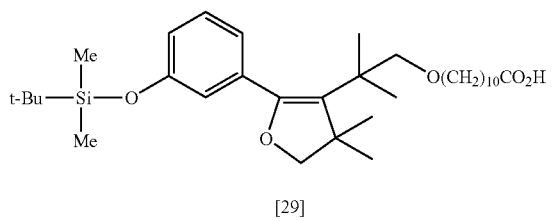

[29]

To a solution having 4-(13-carbonyl-1,1-dimethyl-3-oxatridecan-1-yl)-5-(3-hydroxyphenyl)-3,3-dimethyl-2,3-dihydrofuran (compound (21)) (553 mg, 1.24 mmol) dissolved in anhydrous DMF (6 mL) in a nitrogen atmosphere at room temperature, imidazole (257 mg, 3.77 mmol) and chlorinated t-butyldimethylsilane (566 mg, 3.76 mmol) were added, followed by stirring for 1.5 hours. The reaction mixture was put into a saturated ammonium chloride aqueous solution and extracted with ethyl acetate. The organic layer was washed with a saturated sodium chloride aqueous solution, dried over anhydrous magnesium sulfate and then concentrated. The concentrate was put into a silica gel column and developed with a mixed solvent of hexane and ethyl acetate (2:1), whereby 5-(3-t-butyldimethylsiloxyphenyl)-4-(13-carboxy-1,1-dimethyl-3-oxatridecan-1-yl)-3,3-dimethyl-2,3-dihydrofuran (compound (29)) was obtained as a colorless oil in an amount of 607 mg in a yield of 87.4%.

$^1$H-NMR (400 Hz, CDCl$_3$) $\delta_H$ 0.18 (s, 6H), 0.98 (s, 9H), 1.03 (s, 6H), 1.27–1.30 (m, 18H), 1.47–1.52 (m, 2H), 1.63 (quintet, J=7.2 Hz, 2H), 2.34 (t, J=7.6 Hz, 2H). 3.10 (s, 2H), 3.24 (t, J=6.8 Hz, 2H), 3.86 (s, 2H), 6.76–6.79 (m, 2H), 6.90 (d with fine coupling, J=7.6 Hz, 1H), 7.16 (t with fine coupling, J=7.2 Hz, 1H) ppm.

EXAMPLE 29

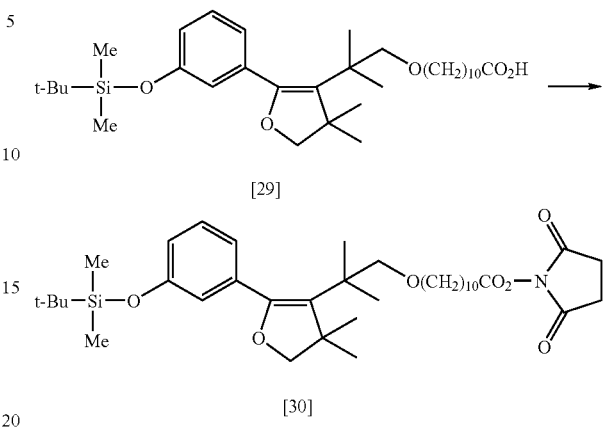

To a solution having 5-(3-t-butyldimethylsiloxyphenyl)-4-(13-carboxy-1,1-dimethyl-3-oxatridecan-1-yl)-3,3-dimethyl-2,3-dihydrofuran (compound (29)) (405 mg, 0.722 mmol) dissolved in anhydrous acetonitrile (5 mL) in a nitrogen atmosphere at room temperature, di(N-succinimidyl)carbonate (237 mg, 0.925 mmol) and triethylamine (one drop) were added, followed by stirring for 50 minutes. The reaction solution was concentrated, and the concentrate was put into a silica gel column and developed with a mixed solvent of hexane and ethyl acetate (2:1), whereby 5-(3-t-butyldimethylsiloxyphenyl)-3,3-dimethyl-4-(1,1-dimethyl-13-succinimidoxycarbonyl-3-oxatridecan-1-yl)-2,3-dihydrofuran (compound (30)) was obtained as a colorless oil in an amount of 431 mg in a yield of 90.5%.

$^1$H-NMR (400 Hz, CDCl$_3$) $\delta_H$ 0.18 (s, 6H), 0.98 (s, 9H), 1.03 (s, 6H), 1.28–1.31 (m, 18H), 1.49–1.54 (m, 2H), 1.74 (quintet, J=7.6 Hz, 2H), 2.59 (t, J=7.6 Hz, 2H), 2.82 (s, 4H), 3.11 (s, 2H), 3.24 (t, J=6.8 Hz, 2H), 3.86 (s, 2H), 6.76–6.79 (m, 2H), 6.90 (d, J=7.6 Hz, 1H), 7.16 (t with fine coupling, J=7.2 Hz, 1H) ppm.

EXAMPLE 30

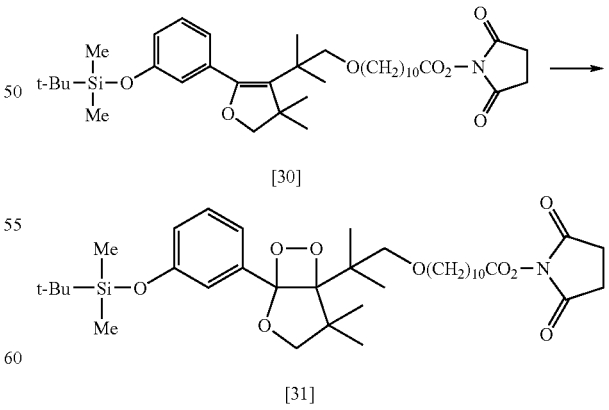

5-(3-t-butyldimethylsiloxyphenyl)-3,3-dimethyl-4-(1,1-dimethyl-13-succinimidoxycarbonyl-3-oxatridecan-1-yl)-2,3-dihydrofuran (compound (30)) (177 mg, 0.269 mmol) and TPP (0.8 mg) were added to dichloromethane (15 mL), and the mixture was irradiated with visible light by a 940 W sodium lamp in an oxygen atmosphere at 0° C. for 1.5 hours. The reaction mixture was concentrated, and the concentrate was put into a silica gel column and developed with a mixed solvent of hexane and ethyl acetate (2:1), whereby 1-(3-t-butyldimethylsiloxyphenyl)-4,4-dimethyl-5-(1,1-dimethyl-13-succinimidoxycarbonyl-3-oxatridecan-1-yl)-2,6,7-trioxabicyclo[3.2.0]heptane (compound (31)) was obtained in an amount of 181 mg in a yield of 97.5%.

$^1$H-NMR (400 Hz, CDCl$_3$) δ$_H$ 0.19 (s, 6H), 0.87 (s, 3H), 0.98 (s, 9H), 1.14 (s, 3H), 1.16 (s, 3H). 1.26–1.40 (m, 12H), 1.38 (s, 3H), 1.46–1.50 (m, 2H), 1.74 (quintet, J=7.6 Hz, 2H), 2.60 (t, J=7.6 Hz, 2H), 2.82 (s, 4H), 3.22–3.29 (m, 4H), 3.80 (d, J=8.4 Hz, 1H), 4.57 (d, J=8.0 Hz, 1H), 6.84–6.87 (m, 1H), 7.11 (s, 1H), 7.12–7.25 (m, 2H) ppm.

EXAMPLE 31

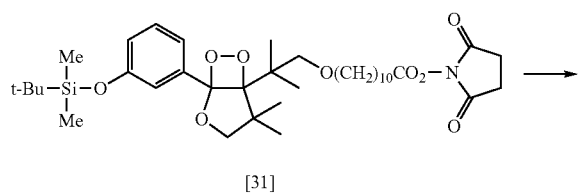

[31]

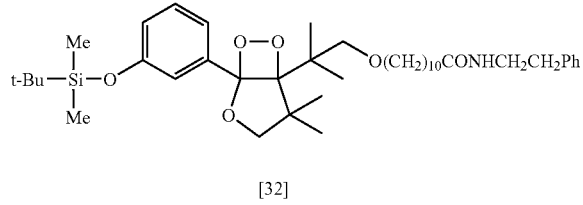

[32]

To a solution having 1-(3-t-butyldimethylsiloxyphenyl)-4,4-dimethyl-5-(1,1-dimethyl-13-succinimidoxycarbonyl-3-oxatridecan-1-yl)-2,6,7-trioxabicyclo[3.2.0]heptane (53.7 mg, 0.0778 mmol) (compound (31)) dissolved in anhydrous dichloromethane (1 mL) in a nitrogen atmosphere at 0° C., β-phenetylamine (11 mg, 0.0908 mmol) dissolved in anhydrous dichloromethane (1 mL), was added, followed by stirring for one hour and 20 minutes. To the reaction solution, β-phenetylamine (5 mg, 0.0413 mmol) dissolved in anhydrous dichloromethane (0.5 mL), was further added, followed by stirring for 30 minutes. The reaction mixture was concentrated, and the concentrate was put into a silica gel column and developed with a mixed solvent of hexane and ethyl acetate (1:1), whereby 1-(3-t-butyldimethylsiloxyphenyl)-4,4-dimethyl-5-[1,1-dimethyl-13-(2-phenylethylcarbamoyl)-3-oxatridecan-1-yl]-2,6,7-trioxabicyclo[3.2.0] heptane (compound (32)) was obtained in an amount of 51.8 mg in a yield of 95.6%.

$^1$H-NMR (400 Hz, CDCl$_3$) δ$_H$ 0.19 (s, 6H), 0.86 (s, 3H), 0.98 (s, 9H), 1.14 (s, 3H), 1.16 (s, 3H), 1.24–1.40 (m, 12H), 1.38 (s, 3H), 1.45–1.50 (m, 2H), 1.52–1.60 (m, 2H), 2.11 (t, J=7.6 Hz, 2H), 2.81 (t, J=6.8 Hz, 2H), 3.22–3.29 (m, 4H), 3.52 (q, J=6.8 Hz, 2H), 3.80 (d, J=8.4 Hz, 1H), 4.57 (d, J=8.0 Hz, 1H), 6.84–6.87 (m, 1H), 7.11 (s, 1H), 7.18–7.33 (m, 7H) ppm.

EXAMPLE 32

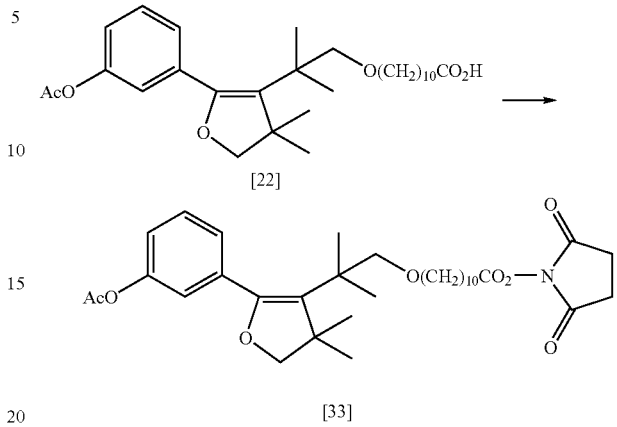

To a solution having 5-(3-acetoxyphenyl)-4-(13-carboxy-1,1-dimethyl-3-oxatridecan-1-yl)-3,3-dimethyl-2,3-dihydrofuran (192 mg, 0.393 mmol) (compound (22)) dissolved in anhydrous acetonitrile (3 mL) in a nitrogen atmosphere at room temperature, di(N-succinimidyl)carbonate (125 mg, 0.488 mmol) and triethylamine (one drop) were added, followed by stirring for 1.5 hours. The reaction solution was concentrated, and the concentrate was put into a silica gel column and developed with a mixed solvent of hexane and ethyl acetate (2:1), whereby 5-(3-acetoxyphenyl)-3,3-dimethyl-4-(1,1-dimethyl-13-succinimidoxycarbonyl-3-oxatridecan-1-yl)-2,3-dihydrofuran (compound (33)) was obtained as a colorless oil in an amount of 191 mg in a yield of 83.0%.

$^1$H-NMR (400 Hz, CDCl$_3$) δ$_H$ 1.03 (s, 6H), 1.26–1.42 (m, 18H), 1.47–1.52 (m, 2H), 1.73 (quintet, J=7.6 Hz, 2H), 2.27 (s, 3H), 2.59 (t, J=7.6 Hz, 2H), 2.80 (s, 4H), 3.08 (s, 2H), 3.23 (t, J=6.8 Hz, 2H), 3.85 (s, 2H), 7.03–7.09 (m, 2H), 7.19 (d with fine coupling, J=7.6 Hz, 1H), 7.31 (t, J=7.6 Hz, 1H) ppm.

EXAMPLE 33

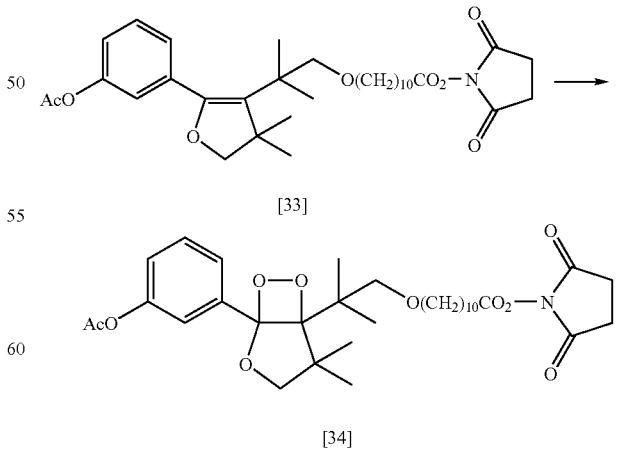

5-(3-acetoxyphenyl)-3,3-dimethyl-4-(1,1-dimethyl-13-succinimidoxycarbonyl-3-oxatridecan-1-yl)-2,3-dihydrofuran (compound (33)) (100 mg, 0.171 mmol) and TPP (0.8 mg) were added to dichloromethane (10 mL), and the mixture was irradiated with visible light by a 940 W sodium lamp in an oxygen atmosphere at 0° C. for one hour. The reaction mixture was concentrated, and the concentrate was put into a silica gel column and developed with a mixed solvent of hexane and ethyl acetate (3:2), whereby 1-(3-acetoxyphenyl)-4,4-dimethyl-5-(1,1-dimethyl-13-succinimidoxycarbonyl-3-oxatridecan-1-yl)-2,6,7-trioxabicyclo[3.2.0]heptane (compound (34)) was obtained in an amount of 87 mg in a yield of 82.5%.

$^1$H-NMR (400 Hz, CDCl$_3$) $\delta_H$ 0.86 (s, 3H), 1.15 (s, 3H), 1.16 (s, 3H), 1.24–1.40 (m, 12H), 1.39 (s, 3H), 1.46–1.50 (m, 2H), 1.74 (quintet, J=7.6 Hz, 2H), 2.30 (s, 3H), 2.60 (t, J=7.6 Hz, 2H), 2.83 (s, 4H), 3.23 (s, 2H), 3.27 (t with fine coupling, J=6.8 Hz, 2H), 3.81 (d, J=8.0 Hz, 1H), 4.58 (d, J=8.0 Hz, 1H), 7.12–7.15 (m, 1H), 7.37 (s, 1H), 7.40 (t, J=7.6 Hz, 1H), 7.51 (d, J=7.2 Hz, 1H) ppm.

EXAMPLE 34

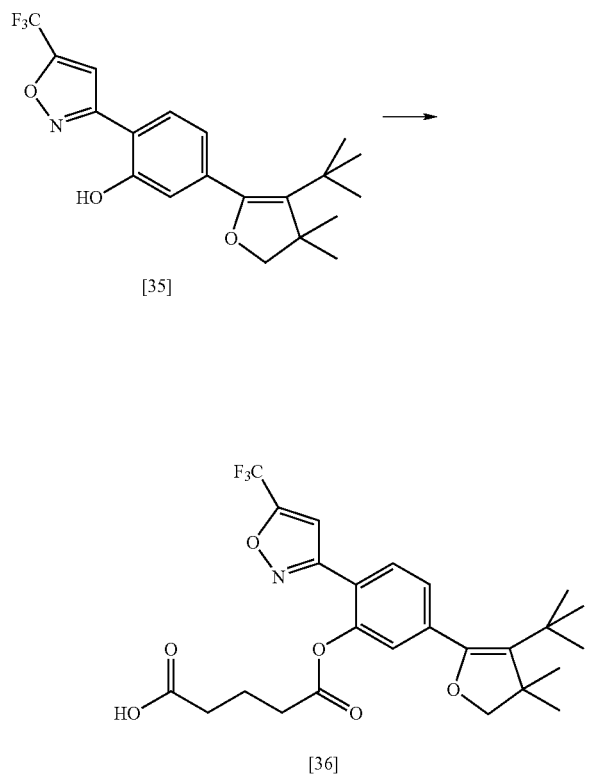

To a solution having 5-(3-t-butyl-4,4-dimethyl-4,5-dihydrofuran-2-yl)-2-(5-trifluoromethylisooxazol-3-yl)phenol (compound (35)) (500 mg, 1.31 mmol) as a known compound disclosed in JP-A-2002-338576, dissolved in pyridine (100 mL) at room temperature, DMAP (20 mg) and glutaric anhydride (1.496 g, 13.11 mmol) were added, followed by stirring for two hours at 100° C. The reaction mixture was put into a 1N hydrochloric acid aqueous solution and extracted with ethyl acetate. The organic layer was washed with a saturated sodium chloride aqueous solution, dried over anhydrous magnesium sulfate and then concentrated. The concentrate was put into a silica gel column and developed with a mixed solvent of hexane and ethyl acetate (1:1), whereby 5-(3-t-butyl-4,4-dimethyl-4,5-dihydrofuran-2-yl)-2-(5-trifluoromethylisooxazol-3-yl)phenyl gultarate (compound (36)) was obtained as a white solid in an amount of 510 mg in a yield of 87.5%.

$^1$H-NMR (500 Hz, CDCl$_3$) $\delta_H$ 1.07 (s, 9H), 1.34 (s, 6H), 2.11 (quintet, J=7.0 Hz, 2H), 2.57 (t, J=7.5 Hz, 2H), 2.79 (t, J=7.5 Hz, 2H), 3.89 (s, 2H), 7.16 (d, J=1.0 Hz, 1H), 7.34 (dd, J=8.3 and 1.5 Hz, 1H), 7.55 (d, J=1.0 Hz, 1H), 8.10 (d, J=7.5 Hz, 1H) ppm.

EXAMPLE 35

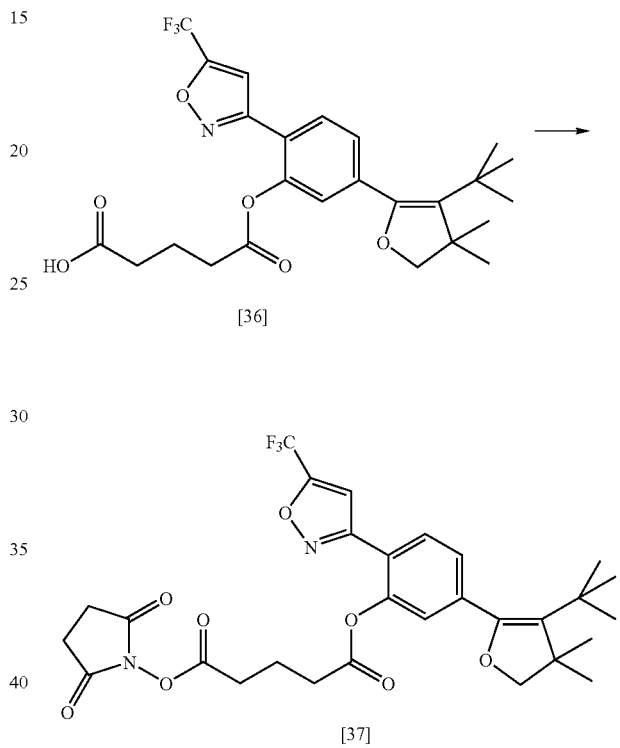

To a solution having 5-(3-t-butyl-4,4-dimethyl-4,5-dihydrofuran-2-yl)-2-(5-trifluoromethylisooxazol-3-yl)phenyl gultarate (compound (36)) (510 mg, 1.03 mmol) dissolved in DMF (10 mL) at 0° C., N-hydroxysuccinimide (179 mg, 1.55 mmol) and 1-ethyl-3-(3-dimethylaminopropyl)carbodiimide hydrochloride (302 mg, 1.57 mmol) were added, followed by stirring at 4° C. overnight. The reaction mixture was put into a saturated sodium chloride aqueous solution and extracted with ethyl acetate. The organic layer was washed with a saturated sodium chloride aqueous solution, dried over anhydrous magnesium sulfate and then concentrated. The concentrate was put into a silica gel column and developed with a mixed solvent of hexane and ethyl acetate (1:1), whereby 5-(3-t-butyl-4,4-dimethyl-4,5-dihydrofuran-2-yl)-2-(5-trifluoromethylisooxazol-3-yl)phenylsuccinimidyl gultarate (compound (37)) was obtained as a white solid in an amount of 515 mg in a yield of 84.4%.

$^1$H-NMR (500 Hz, CDCl$_3$) $\delta_H$ 1.07 (s, 9H), 1.34 (s, 6H), 2.21 (quintet, J=7.0 Hz, 2H), 2.83–2.87 (m, 8H), 3.89 (s, 2H), 7.17 (d, J=1.0 Hz, 1H), 7.34 (dd, J=8.3 and 1.5 Hz, 1H), 7.63 (d, J=1.0 Hz, 1H), 8.10 (d, J=8.5 Hz, 1H) ppm.

EXAMPLE 36

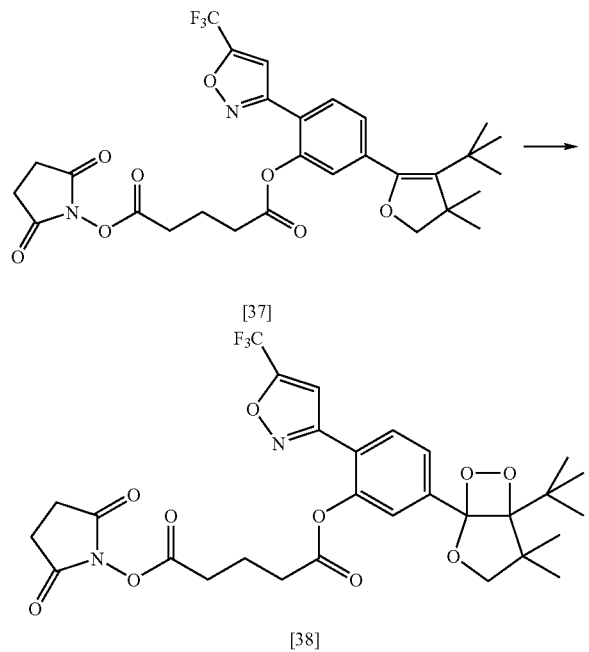

5-(3-t-butyl-4,4-dimethyl-4,5-dihydrofuran-2-yl)-2-(5-trifluoromethylisooxazol-3-yl)phenylsuccinimidyl gultarate (compound (37)) (505 mg, 0.85 mmol) and TPP (15 mg) were added to dichloromethane (15 mL), and the mixture was irradiated with visible light by a 940 W sodium lamp in an oxygen atmosphere at 0° C. for two hours. The reaction mixture was concentrated, and the concentrate was put into a silica gel column and developed with a mixed solvent of hexane and ethyl acetate (1:1), whereby 5-(5-t-butyl-4,4-dimethyl-2,6,7-trioxabicyclo[3.2.0]hept-1-yl)-2-(5-trifluoromethylisooxazol-3-yl)phenylsuccinimidyl gultarate (compound (38)) was obtained as a white solid in an amount of 445 mg in a yield of 83.6%.

$^1$H-NMR (500 Hz, CDCl$_3$) $\delta_H$ 1.00 (s, 9H), 1.17 (s, 3H), 1.39 (s, 3H), 2.22 (quintet, J=7.0 Hz, 2H), 2.83–2.89 (m, 8H), 3.87 (d, J=8.0 Hz, 1H), 4.60 (d, J=8.0 Hz, 1H), 7.49 (s, 1H), 7.65 (dd, J=1.5 Hz, 1H), 7.68 (d, J=9.5 Hz, 1H), 8.17 (d, J=8.0 Hz, 1H) ppm.

EXAMPLE 37

A thyroid stimulating hormone antibody (TSH antibody) was put into a dialysis tube, and dialysis was carried out at from 2 to 8° C. against a 0.1 M phosphate buffer solution (pH 7.0). Using 1 L of the buffer solution per operation, dialysis was carried out for at least 4 hours. After completion of the dialysis, the antibody solution was put into a syringe provided with a 0.45 μm filter, and filtration was carried out. The volume at that time was 0.45 mL, and the concentration was 17.7 mg/mL. Then, a 0.1 M phosphate buffer solution (pH 7.0) was added so that the protein concentration in this antibody solution became 5 mg/mL. This solution was transferred to a reactor and immersed in a constant temperature vessel controlled at a temperature of 4±1° C. for 30 minutes. 0.015 mL of a DMF solution (concentration: 10.4 mg/mL) of 5-(5-t-butyl-4,4-dimethyl-2,6,7-trioxabicyclo[3.2.0]hept-1-yl)-2-(5-trifluoromethylisooxazol-3-yl)phenylsuccinimidyl gultarate (compound (38)) was added. After completion of the dropwise addition, the mixture was gently stirred by means of a vortex, and then stirring was stopped, and the mixture was left to stand at 4±1° C. for 17 hours in the constant temperature vessel. After completion of the reaction, the reaction solution was transferred to a dialysis tube, and dialysis was carried out at from 2 to 8° C. against a 0.1 M phosphoric acid/NaCl buffer solution (0.1% NaN$_3$) (pH 7.0). Using at least 1 L of the buffer solution per operation, dialysis was carried out three times for at least 4 hours. After completion of the dialysis, the antibody solution was put into a syringe provided with a 0.22 μm filter, and filtration was carried out. As a result, 0.88 mL of a chemiluminescent substrate-labeled thyroid stimulating hormone antibody was obtained, and its concentration was 7,599 mA.

EXAMPLE 38

The chemiluminescent substrate-labeled thyroid stimulating hormone antibody prepared in Example 37, was diluted with a 20 mM ACES (0.1% BSA, 0.1% NaN$_3$) buffer solution (pH 6.5) so that the concentration would be 100 mA. To 33 μL of this solution, 200 μL of a 0.5 N sodium hydroxide aqueous solution was added as a trigger, and the luminescence was measured by means of a luminescence measuring apparatus. The obtained luminescence curve is shown in FIG. 1.

The 1,2-dioxetane derivatives (I) and (III) of the present invention are stable as compounds themselves, whereby handling is easy.

Further, the 1,2-dioxetane derivatives (I) and (III) of the present invention can be labeled, for example, to an organic compound or a biological molecule via a part of the group such as X or W in their structures. Accordingly, by bonding them to a substance having a specific affinity, it is possible to obtain an immunoassay reagent of the present invention. By using the immunoassay reagent of the present invention, it is possible to lower the background at the time of the measurement by e.g. an immunoassay. By this effect, measurement with higher sensitivity in e.g. an immunoassay, will be possible.

Further, in the case of a 1,2-dioxetane derivative (I) wherein Z is —OSi(R$_7$R$_8$)— (wherein each of R$_7$ and R$_8$ which are independent of each other, is an alkyl group or an aryl group) or —(R$_9$R$_{10}$)SiO— (wherein each of R$_9$ and R$_{10}$ which are independent of each other, is an alkyl group or an aryl group), and in the case of a 1,2-dioxetane derivative (III), if immunoassay reagents of the present invention are obtained by using them, and they are used to form and detect an immunoreaction product on a solid phase, there will be the following effects. Namely, the portion corresponding to the 1,2-dioxetane derivative in the immunoreaction product formed on the solid phase will be decomposed in the presence of fluorine ions or under an alkaline condition, whereby by virtue of the characteristic due to its structure, the portion having the 1,2-dioxetane structure will be decomposed in such a manner that will be cleaved from the immunoreaction product on the solid phase and it will be discharged into the solution, whereupon luminescence will take place at the same time. Accordingly, the luminescence will take place in the solution i.e. not on the solid phase. Thus, the detection of the luminescence is easy with no substantial noise, whereby measurement with high sensitivity will be possible. Further, the luminescence will not be detected on the solid phase, whereby detection will not be fluctuated by the shape of the solid phase. Thus, the system will be suitable for detecting the luminescence in the liquid phase (homogeneous system) without loss.

The entire disclosures of Japanese Patent Application No. 2002-64040 filed on Mar. 8, 2002, Japanese Patent Application No. 2002-88380 filed on Mar. 27, 2002 and Japanese Patent Application No. 2003-16454 filed on Jan. 24, 2003 including specifications, claims, drawings and summaries are incorporated herein by reference in their entireties.

What is claimed is:

1. A chemiluminescent reagent, comprising: a 1,2-dioxetane derivative of the formula (I):

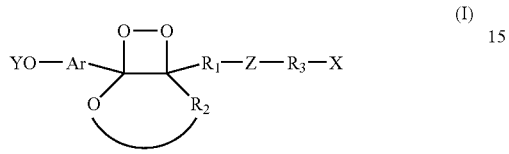

wherein
Ar is an aryl group which may have an alkyl group, an aryl group, a halogen atom, an alkoxyl group, a carboxyl group, a formyl group, an alkyl ester, an aryl ester, an alkylketone, an arylketone or a hetero ring bonded thereto, X is a substituent capable of labeling an organic compound or a biological molecule, or an ester, Y is a hydrogen atom, an acyl group or a group of the formula $-Si(R_4R_5R_6)$, wherein each of $R_4$, $R_5$ and $R_6$ which are independent of one another, is an alkyl group or an aryl group, Z is an alkyl group, an aryl group, an oxygen atom, a sulfur atom, a carbonyl group, $-(CO)-O-$, $-O-(CO)-$, $-NH-$, $-NH-CO-$, $-CO-NH-$, $-OSi(R_7R_8)-$, wherein each of $R_7$ and $R_8$ which are independent of each other, is an alkyl group or aryl group; or a group of the formula $-(R_9R_{10})SiO-$, wherein each of $R_9$ and $R_{10}$ which are independent of each other, is an alkyl group or an aryl group;

each of $R_1$ and $R_2$ is an alkyl group or an aryl group, and $R_3$ is a spacer.

2. An immunoassay reagent, comprising a 1,2-dioxetane derivative of formula (I) bonded via X of formula (I) to an antibody or a receptor:

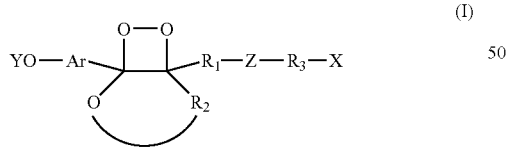

wherein
Ar is an aryl group which may have an alkyl group, an aryl group, a halogen atom, an alkoxyl group, a carboxyl group, a formyl group, an alkyl ester, an aryl ester, an alkylketone, an arylketone or a hetero ring bonded thereto, X is a substituent capable of labeling an organic compound or a biological molecule, or an ester, Y is a hydrogen atom, an acyl group or a group of the formula $-Si(R_4R_5R_6)$, wherein each of $R_4$, $R_5$ and $R_6$ which are independent of one another, is an alkyl group or an aryl group, Z is an alkyl group, an aryl group, an oxygen atom, a sulfur atom, a carbonyl group, $-(CO)-O-$, $-O-(CO)-$, $-NH-$, $-NH-CO-$, $-CO-NH-$, $-OSi(R_7R_8)-$, wherein each of $R_7$ and $R_8$ which are independent of each other, is an alkyl group or aryl group; or a group of the formula $-(R_9R_{10})SiO-$, wherein each of $R_9$ and $R_{10}$ which are independent of each other, is an alkyl group or an aryl group;

each of $R_1$ and $R_2$ is an alkyl group or an aryl group, and $R_3$ is a spacer.

3. An immunoassay reagent, comprising: a 1,2-dioxetane derivative of formula (II) bonded via W of formula (II) to an antibody or a receptor:

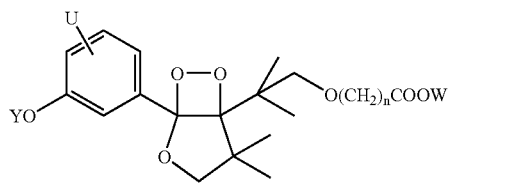

wherein Y is a hydrogen atom, an acyl group or a group of the formula $-Si(R_4R_5R_6)$, wherein each of $R_4$, $R_5$ and $R_6$ which are independent of one another, is an alkyl group or an aryl group, n is an integer of from 1 to 20, W is a hydrogen atom, an alkyl group or a succinimido substituent, and U is a hydrogen atom, an alkyl group, an aryl group, a halogen atom, an alkoxyl group, a carboxyl group, a formyl group, an alkyl ester, an aryl ester, an alkylketone, an arylketone or a hetero ring.

4. A method of detecting a substance, comprising: mixing the immunoassay reagent according to claim 2 and said substance to be detected or a mixture containing said substance to be detected, to obtain a reaction mixture;

reacting said reaction mixture to bond said substance to be detected with said immunoassay reagent; and measuring the amount of immunoassay reagent which was bonded or not bonded to said substance to be detected, wherein said immunoassay reagent is decomposed in the presence of fluorine ions or under an alkaline condition, wherein said decomposition is accompanied by chemiluminescence, and an intensity of said chemiluminescence is measured.

5. The method according to claim 4, wherein said substance to be detected is selected from the group consisting of hormones, cancer-related substances, viral antigens, viral antibodies and nucleic acids.

6. The method according to claim 4, wherein said substance to be detected is selected from the group consisting of hCG, TSH, LH, AFP, CEA, HIV, HTLV-I, DNA and RNA.

7. A method of detecting a substance, comprising:

mixing the immunoassay reagent according to claim 3 and said substance to be detected or a mixture containing said substance to be detected, to obtain a reaction mixture;

reacting said reaction mixture to bond said substance to be detected with said immunoassay reagent; and measuring the amount of immunoassay reagent which was bonded or not bonded to said substance to be detected, wherein said immunoassay reagent is decomposed in the presence of fluorine ions or under an alkaline condition, wherein said decomposition is accompanied by chemiluminescence, and an intensity of said chemiluminescence is measured.

8. The method according to claim 7, wherein said substance to be detected is selected from the group consisting of hormones, cancer-related substances, viral antigens, viral antibodies and nucleic acids.

9. The method according to claim 7, wherein said substance to be detected is selected from the group consisting of hCG, TSH, LH, AFP, CEA, HIV, HTLV-I, DNA and RNA.

* * * * *